(12) United States Patent
Tal et al.

(10) Patent No.: US 10,384,052 B2
(45) Date of Patent: Aug. 20, 2019

(54) GI TRACT STIMULATION DEVICES AND METHODS

(71) Applicant: E-MOTION MEDICAL, LTD., Herzliya (IL)

(72) Inventors: Michael Gabriel Tal, Savyon (IL); Amichay Haim Gross, Herzliya (IL); Yuri Shpolansky, Pardes Hanna-Karkur (IL)

(73) Assignee: E-MOTION MEDICAL, LTD, Tel-Aviv (IL)

( * ) Notice: Subject to any disclaimer, the term of this patent is extended or adjusted under 35 U.S.C. 154(b) by 364 days.

(21) Appl. No.: 14/655,067

(22) PCT Filed: Dec. 20, 2013

(86) PCT No.: PCT/US2013/077261
§ 371 (c)(1),
(2) Date: Jun. 24, 2015

(87) PCT Pub. No.: WO2014/105759
PCT Pub. Date: Jul. 3, 2014

(65) Prior Publication Data
US 2015/0343211 A1    Dec. 3, 2015

Related U.S. Application Data

(60) Provisional application No. 61/745,751, filed on Dec. 24, 2012.

(51) Int. Cl.
*A61N 1/05* (2006.01)
*A61N 1/372* (2006.01)
*A61N 1/36* (2006.01)

(52) U.S. Cl.
CPC ....... *A61N 1/0517* (2013.01); *A61N 1/36007* (2013.01); *A61N 1/3727* (2013.01)

(58) Field of Classification Search
CPC . A61N 1/36007; A61N 1/0517; A61N 1/3727
See application file for complete search history.

(56) References Cited

U.S. PATENT DOCUMENTS 3,128,760 A * 4/1964 Baker ............... A61B 1/00082
600/554
3,411,507 A    11/1968 Wingrove
(Continued)

FOREIGN PATENT DOCUMENTS

JP        2011529766 A    12/2011
WO           9217150       10/1992
(Continued)

OTHER PUBLICATIONS

Jun. 20, 2014 International Search Report issued in International Patent Application No. PCT/US2013/077261.
(Continued)

*Primary Examiner* — Michael D Abreu
(74) *Attorney, Agent, or Firm* — Veros Legal Solutions, LLP

(57) ABSTRACT

Systems, methods and devices, for stimulating one or more esophageal muscle contractions are provided. The system, methods, and devices may be designed to evoke motion and/or restore function in one or more organs that are located distal to the lower esophageal sphincter. A controller and a generator may be used to transmit signals to one or more electrodes in a tube placed in a patient's GI tract. In some aspect, the generator is configures to generate a series of pulses for one or more periods of time. In some aspects, a preliminary pulse is transmitted to narrow and esophageal portion such that an esophageal wall is in contact with at least one electrode thus lowering the nominal stimulation threshold.

19 Claims, 13 Drawing Sheets

(56) References Cited

U.S. PATENT DOCUMENTS

| | | |
|---|---|---|
| 4,735,206 A | 4/1988 | Hewson |
| 5,540,730 A | 7/1996 | Terry et al. |
| 5,690,691 A | 11/1997 | Chen et al. |
| 5,716,385 A | 2/1998 | Mittal et al. |
| 5,725,564 A | 3/1998 | Freed et al. |
| 5,814,092 A | 9/1998 | King |
| 5,836,994 A | 11/1998 | Bourgeois |
| 5,891,185 A | 4/1999 | Freed et al. |
| 6,010,453 A | 1/2000 | Fiddian-Green |
| 6,097,984 A | 8/2000 | Douglas |
| 6,148,222 A | 11/2000 | Ramsey |
| 6,591,137 B1 | 7/2003 | Fischell et al. |
| 6,754,536 B2 | 6/2004 | Swoyer et al. |
| 6,773,452 B2 | 8/2004 | Shaker |
| 6,895,279 B2 | 5/2005 | Loeb et al. |
| 7,167,750 B2 | 1/2007 | Knudson et al. |
| 7,343,201 B2 | 3/2008 | Mintchev |
| 7,402,172 B2 | 7/2008 | Chin et al. |
| 7,416,546 B2 | 8/2008 | Pugsley et al. |
| 7,606,623 B2 | 10/2009 | Ludlow et al. |
| 7,660,636 B2 | 2/2010 | Castel et al. |
| 7,720,539 B2 | 5/2010 | Mintchev |
| 7,738,961 B2 | 6/2010 | Sharma |
| 7,794,425 B2 | 9/2010 | Gobel |
| 8,032,222 B2 | 10/2011 | Loushin et al. |
| 8,092,433 B2 | 1/2012 | Hamdy |
| 8,209,034 B2 | 6/2012 | Simon et al. |
| 8,275,460 B2 | 9/2012 | Loushin et al. |
| 8,447,403 B2 | 5/2013 | Sharma et al. |
| 8,447,404 B2 | 5/2013 | Sharma et al. |
| 8,603,188 B2 | 12/2013 | Behan et al. |
| 8,876,762 B2 | 11/2014 | Dayan et al. |
| 2001/0053920 A1 | 12/2001 | Shaker |
| 2006/0247717 A1 | 11/2006 | Starkebaum |
| 2006/0265021 A1 | 11/2006 | Herbert et al. |
| 2007/0073361 A1 | 3/2007 | Goren et al. |
| 2007/0185540 A1 | 8/2007 | Ben-Haim et al. |
| 2007/0225576 A1 | 9/2007 | Brown et al. |
| 2007/0225617 A1 | 9/2007 | Mabary et al. |
| 2007/0293926 A1 | 12/2007 | Dunlay et al. |
| 2008/0009810 A1 | 1/2008 | Hamdy |
| 2008/0167675 A1 | 7/2008 | Hogosta et al. |
| 2008/0249507 A1 | 10/2008 | Hadani |
| 2008/0312712 A1 | 12/2008 | Penner |
| 2008/0319504 A1 | 12/2008 | Loushin et al. |
| 2009/0018602 A1 | 1/2009 | Mitelberg et al. |
| 2009/0030475 A1 | 1/2009 | Brynelsen et al. |
| 2009/0062725 A1 | 3/2009 | Goebel |
| 2009/0132001 A1 | 5/2009 | Soifer et al. |
| 2009/0143651 A1 | 6/2009 | Kallback et al. |
| 2009/0259274 A1 | 10/2009 | Simon et al. |
| 2010/0030133 A1 | 2/2010 | Elia et al. |
| 2010/0087715 A1 | 4/2010 | Bommel et al. |
| 2010/0160996 A1 | 6/2010 | Simon et al. |
| 2010/0217368 A1 | 8/2010 | Dinsmoor et al. |
| 2010/0241191 A1 | 9/2010 | Testerman et al. |
| 2010/0305655 A1 | 12/2010 | Raffle et al. |
| 2011/0004266 A1* | 1/2011 | Sharma ............ A61N 1/36007 607/40 |
| 2011/0034967 A1* | 2/2011 | Chen ................ A61N 1/0509 607/40 |
| 2011/0130650 A1 | 6/2011 | Dayan et al. |
| 2011/0144481 A1 | 6/2011 | Feer et al. |
| 2013/0012920 A1 | 1/2013 | Elia et al. |
| 2013/0014761 A1 | 1/2013 | Elia et al. |
| 2013/0131753 A1 | 5/2013 | Simon et al. |
| 2013/0158514 A1 | 6/2013 | Elia et al. |
| 2013/0197321 A1 | 8/2013 | Wilson |
| 2013/0231753 A1 | 9/2013 | Liddy et al. |
| 2014/0236262 A1 | 8/2014 | You et al. |
| 2014/0330076 A1 | 11/2014 | Elia et al. |

FOREIGN PATENT DOCUMENTS

| | | |
|---|---|---|
| WO | 2005007120 A2 | 1/2005 |
| WO | 2005051486 A1 | 6/2005 |
| WO | 2006060458 A1 | 6/2006 |
| WO | 2008088985 A2 | 7/2008 |
| WO | 2008104982 A2 | 9/2008 |
| WO | 2010016054 A1 | 2/2010 |
| WO | 2012131303 A1 | 10/2012 |
| WO | 2014009950 A1 | 1/2014 |
| WO | 2014041532 A1 | 3/2014 |
| WO | 2014105759 A1 | 7/2014 |

OTHER PUBLICATIONS

Jan. 7, 2014 International Preliminary Report on Patentability issued in International Patent Application No. PCT/IB2012/001546.

Pellegrini et al., "Gastroesophageal reflux and pulmonary aspiration: Incidence, functional abnormality, and results of surgical therapy," Surgery, vol. 36, No. 1, pp. 110-119.

Guelrud et al., "Transcutaneous Electrical Nerve Stimulation Decreases Lower Esophageal Sphincter Pressure in Patients with Achalasia," Digestive Diseases amd Sciences, vol. 36, No. 8, Aug. 1991, pp. 1029-1033.

Ibanez et al., "Gastroesophageal Reflux in Intubated Patients Receiving Enteral Nutrition: Effect of Supine and Semirecumbent Positions," Journal of Parenteral and Enteral Nutrition, vol. 16, No. 5, pp. 419-422.

Lee et al., "Changes in Gastroesophageal Reflux in Patients With Nasogastric Tube Followed by Percutaneous Endoscopic Gastrostomy," Journal of the Formosan Medical Association, vol. 110, No. 2, pp. 115-119.

Manning et al., "Nasogastric intubation causes gastroesophageal reflux in patients undergoing elective laparotomy," Surgery, vol. 130, No. 5, Mar. 24, 2001, pp. 788-791.

Paterson, William G., "Esophageal peristalsis," PA RT 1 Oral cavity, pharynx and esophagus, GI Motility online, www.nature.com, May 16, 2006, pp. 1-24.

Torres et al., "Stomach as a source of colonization of the respiratory tract during mechanical ventilation: association with ventilator-associated pneumonia," European Respiratory Journal, Mar. 10, 1996, pp. 1729-1735.

* cited by examiner

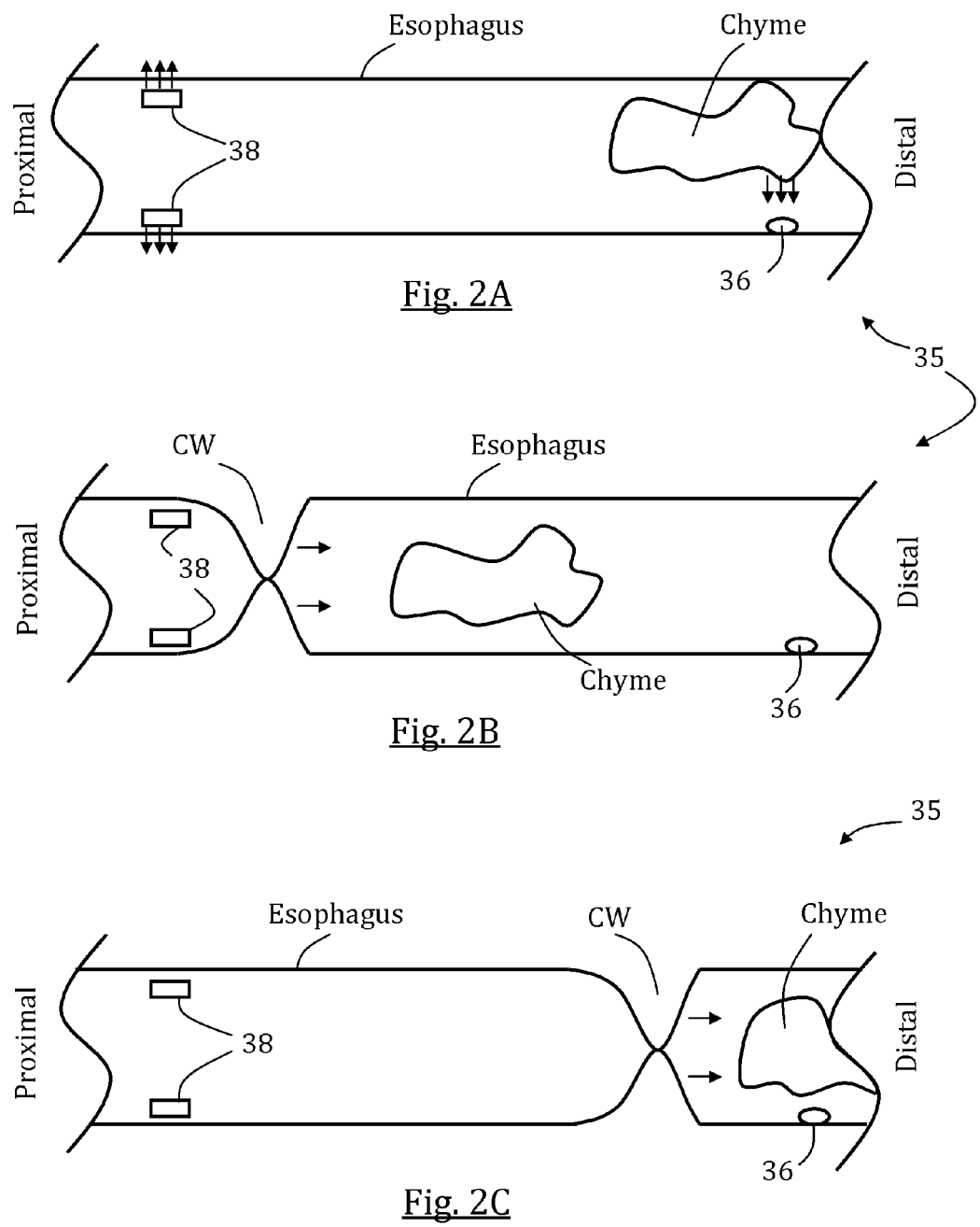

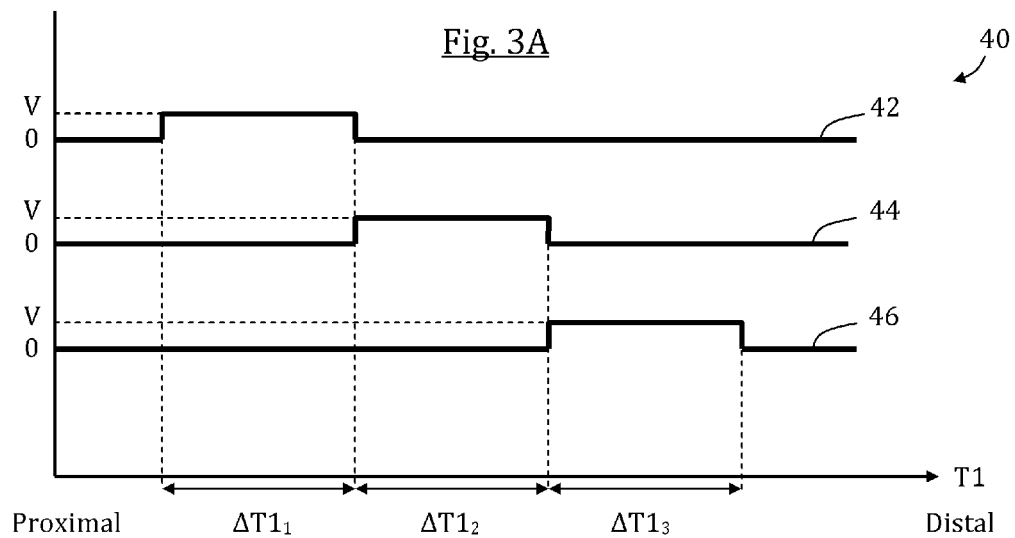
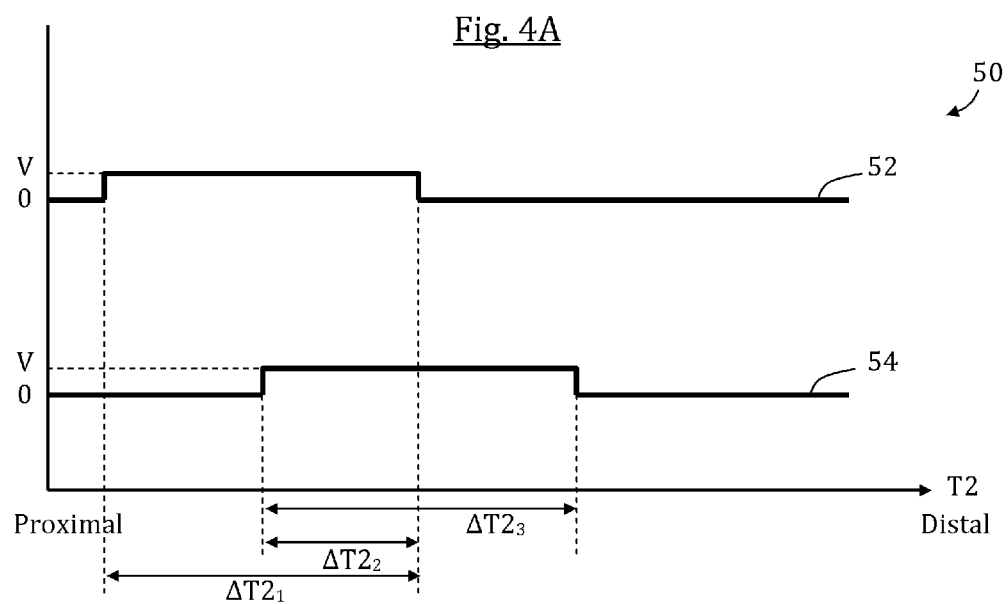

GI TRACT STIMULATION DEVICES AND METHODS

CROSS-REFERENCE TO RELATED APPLICATIONS

This application is a National Phase of PCT Patent Application No. PCT/US2013/077261, having International filing date of Dec. 20, 2013, which claims the benefit of priority under 35 USC § 119(e) of U.S. Provisional Application No. 61/745,751 filed on Dec. 24, 2012. The contents of the above applications are all incorporated by reference as if as fully set forth herein in their entirety.

BACKGROUND

Field of the Invention

The present invention, in some embodiments thereof, relates to devices and methods for initiating and/or sustaining minimal function of at least a portion of the gastrointestinal ("GI") tract, and in particular to devices and methods for generating movement in one or more GI organs, optionally including at least esophageal motility.

Description of the Related Art

Unconscious and anesthetized patients are subject to loss of GI tract function, and specifically GI muscular motility and peristalsis. When patients are in such a condition for prolonged periods (e.g., hours, days or longer) their body cannot properly transfer and digest incoming food, even under external feeding regimes. Therefore, the ability to maintain normal levels of nutrition, immunity, and the ability to fight infections decrease over time. Patients may also encounter long-term deterioration of the GI tract or portions thereof. Additionally or alternatively, patients (e.g., gastroparesis patients) may need to stimulate the GI tract or portions thereof in order to increase current function levels, optionally for rehabilitation of GI tract or as a permanent modifier.

Peristalsis is a sequential, coordinated, contractions wave that travels through portions of the GI tract, such as the esophagus, and the intestines, propelling intraluminal contents distally (generally from mouth to anus). Primary peristalsis is the peristaltic wave triggered by the swallowing center. The peristaltic contractions wave travels at a speed in the order of magnitude of 2 cm/s. The secondary peristaltic wave is induced by esophageal distension from the retained bolus, refluxed material, or swallowed air, with the primary role to clear the esophagus of retained food or any gastroesophageal refluxate. Tertiary contractions are simultaneous, isolated, dysfunctional contractions. Anesthetization, sedation, analgesia, and traumatic events to the body (e.g., shock or surgery) are suspected of causing dysfunction of esophageal peristaltic motility. Hence, gastric content tends to not be transferred distally into the intestine and is even prone to travel up the esophagus, sometimes even all the way to the oral cavity, from where it may infiltrate the respiratory tract.

The esophagus is a tubular muscular organ having a length of approximately 25 cm, located between the upper esophageal sphincter ("UES") and the lower esophageal sphincter ("LES"). The esophagus functions solely to deliver food from the mouth to the stomach using peristaltic muscle motion. Gastric contents refluxing through the esophagus are known to affect conditions which may increase morbidity and mortality rates. Gastroesophageal Reflux ("GER") is a condition, in which the LES opens spontaneously, for varying periods of time, or does not close properly and stomach contents rise up into the esophagus. In Laryngopharyngeal Reflux ("LPR"), the retrograde flow of gastric contents reaches the upper aero-digestive tract. In order to diminish and treat such conditions, efforts have been made to develop medical and surgical means for improving LES functionality and for creating a substitute sphincter proximally adjacent the stomach. In some occasions it may be advantageous to develop a second "line of defense" provided proximally to the LES along the esophagus, especially to push back any gastric contents or chyme that infiltrated the LES or any substitute or supplement thereof. Such a need may arise, for example, in cases of intubation and/or ventilation, usually in anesthetized ICU patients, CVA patients, or others, in which esophageal motility is muted or less dominant.

Tubefeeding (e.g., "gastric feeding" or "enteral feeding") is a common and life preserving procedure, however complications can arise. GER is commonly associated with tubefeeding, including in usage of nasogastric tubing ("NGT") and other gastric feeding practices. Research in past years has discussed the emergence of GER as an effect of the use of NGT (see for example in Ibanez et al., "Gastroesophageal reflux in intubated patients receiving enteral nutrition: effect of supine and semirecumbent positions", *JPEN J Parenter Enteral Nutr.* 1992 September-October; 16(5):419-22; in Manning et al., "Nasogastric intubation causes gastroesophageal reflux in patients undergoing elective laparotomy", *Surgery.* 2001 November; 130(5):788-91; and in Lee et al., "Changes in gastroesophageal reflux in patients with nasogastric tube followed by percutaneous endoscopic gastrostomy", *J Formos Med Assoc.* 2011 February; 110(2):115-9).

SUMMARY

According to an aspect of some embodiments of the present invention, there is provided a system for evoking motion in a GI tract portion including an esophagus. In some embodiments, the system is configured for unconscious or anesthetized patients with dysfunctional GI tract motility and can be used for hours or days, either continuously or in different sessions. Optionally and alternatively, the system can be used as a possible non-implantable solution for chronic gastroparesis (idiopathic or otherwise), optionally for several hours per day, for promoting motility, supporting GI tract function and enabling improved digestion. In some embodiments, the system includes an elongated member sized and configured for nasal or oral placement in the GI tract portion. The system may include a feeding tube, such as nasogastric or nasojejunal. The system includes a series of electrodes mounted or mountable on the elongated member, positioned to stimulate a series of portions of the GI tract portion to evoke local contractions. In some embodiments, the series of electrodes are positioned to stimulate a series of portions of the esophagus between the UES and the LES to evoke local contractions.

In some embodiments, the system includes a generator connected to the series of electrodes. In some embodiments, the system includes a controller comprising a processor and a memory. The controller and generator may be provided as distinct units or as a unitary unit. In some embodiments, the memory includes preset commands for activating the generator to generate a signal sequence such that a second electrode applies a second signal a first time period following a first signal applied by a first electrode positioned proximally thereto, and a second time period preceding a third signal applied by a third electrode positioned distally thereto. In some embodiments, the signal sequence is chosen to evoke motility in a target GI tract portion located distally to the LES. In some embodiments, the target GI tract portion is located in at least one of the stomach, the small intestine, and the large intestine. In some embodiments, each of the electrodes is part of a distinct group of electrodes (e.g., a terminal), optionally a pair of electrodes. Optionally, each group of electrodes includes at least one electrode with a first polarity (e.g., positive) and at least a second electrode with a second polarity (e.g., negative).

In some such embodiments, the generator is configured to generate a series of pulses, including at least one preliminary pulse for initiating narrowing, collapsing, or tightening of an esophageal portion such that an esophageal wall is in contact with at least one electrode thereby lowering an initial stimulation threshold or increasing the contractile response to a second threshold, followed by stimulatory pulses being equal or lower than the initial stimulation threshold and higher than the second threshold.

In some embodiments, the at least one preliminary pulse is greater in magnitude than a maximal magnitude or an average magnitude of the stimulatory pulses. Optionally and alternatively, the at least one preliminary pulse in smaller in magnitude than a minimal magnitude or an average magnitude of the stimulatory pulses. A plurality of pulses may be applied in a frequency between 5 and 50 Hz, optionally approximately 25 Hz. The width of a pulse in the plurality of pulses may be between about 1 and 20 milliseconds. The signal sequence may include a plurality of pulse trains. An intermission between two pulse trains in a single signal sequence may be between about 0 and 2 seconds, optionally between 0.5 and 1 second. A number of pulse trains may be equal or more than the number of electrodes of same designated polarity that is in use for applying the pulse trains.

In some embodiments, the generator is configured to generate a series of pulse trains comprising at least one heterogeneous series comprising a first train having pulses substantially greater than a first threshold followed by a second train having pulses substantially smaller than the first threshold but substantially greater than a second threshold, after a local minimal stimulation threshold is lowered from the first threshold to the second threshold in response to the first train, and/or at least one heterogeneous train comprising a first pulse substantially smaller than the local minimal stimulation threshold followed by a second pulse substantially greater than the local minimal stimulation threshold.

In some embodiments the systems disclosed herein are configured to provide one or more activating sessions. The activating sessions may include a plurality of signal sequences with sequence intermission between each two adjacent signal sequences. The total duration of a single sequence cycle may include a signal sequence and a following sequence intermission that is between about 0.5 minute and 5 minutes or optionally between about 1 minute and 2 minutes. The sessions may be programmed such that sequence cycles during patient feeding are shorter than sequence cycles in between feedings. The sessions may be programmed such that sequence cycles at night time are shorter than sequence cycles at day time.

In some embodiments, the system includes a measuring unit configured for measuring a local condition in direct contact with and/or adjacent at least one of said terminals. Optionally, the local condition includes at least one of pressure, impedance, and pH. In some embodiments, a controller is configured for selecting a pulse magnitude in accordance with said local condition.

In an aspect of some embodiments there is provided a method, which includes at least one of the following steps (not necessarily in same order): (1) positioning the system in a GI tract portion, (2) detecting a local condition, (3) selecting a stimulation magnitude in accordance to the local condition, and (4) stimulating a tissue in direct contact with and/or adjacent at least one of the terminals with said stimulation magnitude.

In some embodiments, the system is configured for evoking esophageal motion. In some embodiments, the esophageal motion includes at least one local contraction. In some such embodiments, at least one local contraction decreases a local segment of the esophagus lumen, optionally to at least 50% its initial diameter. In another embodiment, the at least one local contraction fully closes a local segment of the esophagus. In some embodiments, at least one local contraction develops a local esophageal pressure of at least 15 mmHg, optionally at least 25 mmHg, optionally at least 40 mmHg, or higher, or lower or intermediate to said values.

In some embodiments, the esophageal motion is a patterned motion including at least two evoked contractions at different esophageal portions. Optionally, the different esophageal portions include adjacent esophageal portions and/or remote esophageal portions. In some embodiments, the at least two evoked contractions are sequentially and/or timely generated according to a preset sequence. In some embodiments, the esophageal motion includes distally progressing esophageal contractions (i.e., contractions wave), optionally though not necessarily including peristalsis.

In some embodiments, the system further includes at least one stimulator mounted or mountable on the elongated member, adapted to stimulate a chosen portion of the esophagus to evoke a local shaped contractive reaction. In some embodiments, the at least one stimulator includes at least two stimulators sequentially positioned along an esophageal length; each stimulator is configured to stimulate a different esophageal portion. Optionally, a plurality of stimulators is provided along the effective length of the medical intubation device.

In some embodiments, the at least one stimulator includes an electrode, or a plurality of electrodes, for allowing local electrical stimulation(s) of muscle tissue and/or neural tissue, adjacent and/or in direct contact. The electrode(s) may be shaped as chosen or needed, as known in the relevant art, and may be, for example, circular, rectangular, or ring shaped.

In some embodiments, the system further includes a generator connected to the at least one stimulator. The generator may be provided outside the patient body or alternatively be sized and configured for prolonged intra-oral or intra-esophageal placement. The generator may be an electrical signal generator adapted to generate electrical stimulations via at least one electrode or at least two electrodes electrically connected thereto. Alternatively, the generator may include a pump for cases of inflatable stimulators. The generator may be a pulse generator and/or may be able to generate different shaped signals, for example a step wave, a sine wave, a saw-tooth wave, a variable width pulse or any combination thereof. The generator may include or be connectable to a power source, which may or may not comprise an element of the system. In some embodiments, the power source may be sized and configured for prolonged intra-oral or intra-esophageal placement.

In some embodiments of the invention, the system further includes at least one sensor mounted or mountable on the elongated member. The at least one sensor may be mounted distally to a distal-most stimulator. Optionally, a proximal-most sensor is positioned at least 5 cm distally to the distal-most stimulator, optionally at least 10 cm, optionally approximately 20 cm, or higher, or lower, or intermediate to said values. In some embodiments, the at least one sensor comprises at least one of: a pH sensor, a pressure sensor, a manometer, an impedance sensor, a motion sensor, a capacitance sensor, and a mechanical sensor.

In an aspect of some embodiments, there is provided a method for generating esophageal motion. In some embodiments, the method comprises a step of positioning at least two electrodes, including a proximally positioned electrode and a distally positioned electrode, at distant portions along the esophagus. Optionally, the method includes also a step of electrically connecting the at least two electrodes to a generator. Optionally, the method further includes a step of generating a signal sequence including a first signal at the proximally positioned electrode thereby stimulating a proximal esophageal tissue and a second signal at the distally positioned electrode thereby stimulating a distal esophageal tissue. In some embodiments, the signal sequence produces a contractions wave that travels a length of the esophagus.

Optionally, additionally or alternatively, a method for generating esophageal motion with the system will include a step of placing in an esophagus the elongated member and at least one electrode mountable thereon, and generating at least one stimulating signal to evoke a local shaped contractive reaction. The local shaped contractive reaction may be a spasm, a full contraction, a partial contraction, a peristalsis or any combination thereof.

In an aspect of some embodiments, there is provided a method of initiating muscle movement in at least a portion of the lower gastrointestinal tract, the method comprising at least one of the following steps (not necessarily in same order): (1) guiding a naso-intestinal tube having an electrode into a patient at least until a portion of the naso-intestinal tube extends into the patient's duodenum, (2) electrically connecting the electrode to a signal generator, and (3) generating a signal sequence at the electrode to stimulate a muscle contraction within a portion of the patient's lower gastrointestinal tract. In some embodiments, the electrode is positioned within the patient's duodenum or jejunum, or optionally within the patient's esophagus.

In some embodiments, the step of generating a signal sequence at the electrode induces a muscle contraction in the patient's large intestine and/or stimulates a distally traveling wave of muscle contractions. Optionally, the distally traveling wave includes peristalsis. Optionally, alternatively or additionally, the step of generating a signal sequence at the electrode comprises generating a signal sequence at a plurality of electrodes to evoke at least two contractions at different locations in the lower gastrointestinal tract. Optionally, the different locations in the lower gastrointestinal tract include adjacent locations in the patient's small intestine and/or remote locations in the patient's small intestine and/or the large intestine. Optionally, the at least two evoked contractions are sequentially and/or timely generated according to a preset sequence. In some embodiments, the evoked contractions are configured (e.g., by shape, magnitude, frequency and/or others) for generating or at least improving motility of esophageal content (e.g., bolus or refluxate) distally towards the stomach.

In an aspect of some embodiments there is provided a method for initiating muscle movement in at least a portion of the lower gastrointestinal tract, the method comprising at least one of the following steps (not necessarily in same order): (1) positioning in a patient's esophagus a GI contraction-stimulation system comprising an elongated tube having an electrode pair, (2) electrically connecting a first electrode of the electrode pair to a signal generator, (3) electrically connecting a second electrode of the electrode pair to a grounding site, and (4) powering on the GI contraction-stimulation system, wherein powering on the GI contraction-stimulation system causes the system to generate a signal sequence at the electrode pair to evoke a muscle contraction within at least a portion of the patient's lower gastrointestinal tract.

In some embodiments, the step of powering on the GI contraction-stimulation system further causes the GI contraction-stimulation system to detect a change in impedance between the first electrode and the second electrode, and wherein the GI contraction-stimulation system waits to generate a signal sequence at the electrode pair at least until the detected impedance exceeds a threshold value.

In an aspect of some embodiments, there is provided a system for stimulating muscle contractions within the small intestine. In some embodiments, the system comprising a tubular member sized and configured to extend through a patient's mouth or nose to at least the patient's duodenum. Optionally, the tubular member is a feeding tube.

In some embodiments, the system includes an electrode mounted or mountable on the tubular member. Optionally, the electrode configured and positioned to apply an electrical pulse to a portion of the patient's small intestine to evoke a muscle contraction. In some embodiments, the system includes an electrode configured and positioned to apply an electrical pulse to a portion of the patient's stomach and/or esophagus. In some embodiments, the electrode is part of a group of electrodes, including an electrode pair. Optionally, at least one electrode in a group has a first polarity and at least one other electrode has an opposite polarity. Optionally, the system includes a plurality of electrodes spaced along a length of the tubular member, wherein a distance of less than 5 cm exists between at least two of the plurality of electrodes, and wherein a distance greater than 10 cm exists between a most proximal electrode and a most distal electrode.

In some embodiments, the system includes a generator configured to electrically connect to the electrode. Optionally, the generator is sized and configured for prolonged intra-oral or intra-esophageal placement. Optionally, the generator is a signal (e.g., pulse) generator, and may be referred to as a "stimulation generator."

In some embodiments, the system includes a power source. Optionally, the power source is sized and configured for prolonged intra-oral or intra-esophageal placement.

In some embodiments, the system includes an array of switches coupled to the plurality of electrodes, wherein each of the plurality of electrodes is selectively connected electrically to a signal generator, connected electrically to a grounding site, or disconnected. The plurality of electrodes is optionally arranged into a plurality of terminals, wherein each of the plurality of terminals comprises 2 or 3 electrodes. Optionally, each of the plurality of terminals has one positive electrode and one negative electrode. Optionally, each of the plurality of terminals comprises two negative electrodes and one positive electrode, with the one positive electrode positioned between the two negative electrodes. In some embodiments, the plurality of terminals is positioned such that an intra-terminal distance between each electrode within a terminal is shorter than an inter-terminal distance between each of the plurality of terminals.

In an aspect of some embodiments there is provided a system including an elongated member configured for placement in the esophagus and extending between the UES and LES, or optionally at least between the nasal cavity or oral cavity and at least the stomach, optionally the duodenum, optionally the jejunum. A plurality of electrode sets or terminals are provided along the length of the elongated member so that different portions of the GI tract can be separately evoked to contract by electrical stimulation(s). In some embodiments, at least some of the electrodes and/or terminals are additionally or alternatively applied for measuring, sensing, and/or monitoring, optionally discretely. By individually measuring impedance and controlling each electrode set or terminal, the system can be configured and/or used to effectively function disregarding specific and/or predefined and precise placement and positioning. Optionally, the system is configured to read impedance separately on each terminal and enable stimulation only to terminal(s) that read impedance measurements correlative to certain tissue specific figures, for example a mucosal tissue. Optionally, alternatively or additionally, the system is configured to generate stimuli only at terminals beginning sequentially 2 or 3 terminals away from a distal most terminal reading a below-threshold impedance, therefore optionally, avoiding stimuli of nasal tissue. Another advantage of selective and/or individual terminals control is by enabling improved energy efficiency, since that terminals in poor contact (for example if located in the stomach when the elongated extends therealong without touching stomach walls), can be kept from transferring stimuli.

In case that the system is configured for correlation between impedance and pressure, locally adjacent each terminal, then a controller provided with the system can be configured to work in close-loop so that stimulation magnitude can be set and adjusted separately for each terminal.

In an aspect of some embodiments, there is provided an impedance measuring unit for measuring change of impedance in the esophagus above (i.e., proximally to) the LES, and optionally specifically a portion of the esophagus between the UES and LES. In some embodiments, the impedance measuring unit is provided an integral part of the esophageal/GI stimulatory unit and/or the elongated member (e.g., feeding tube) and in some other embodiments it can be provided separately thereto or instead it (so, for example, only at a change of impedance to certain levels, the stimulation unit may be deployed). In some embodiments, the impedance measuring unit is set to alarm medical personnel when above a threshold value which is in correlation with presence of refluxate. Optionally, the threshold is patient-specific and determined according to impedance measurements taken before from the patient, or it can be based on statistical data of group characteristics correlating with a patient.

In an aspect of some embodiments, a method may comprise positioning, in a GI tract portion, a system comprising an elongated member sized and configured for nasal or oral placement in the esophagus. The elongated member may include a series of electrodes mounted or mountable on said elongated member. The electrodes may be positioned to stimulate a series of portions of the esophagus between the UES and the LES to evoke local contractions of the esophagus. In some embodiments, no electrodes are positioned within the patient's lower gastrointestinal tract. A measuring unit may be configured to measure at least one local condition in direct contact with and/or adjacent to at least one of the electrodes. The local condition may comprise a change in local impedance. The change in local impedance may be indicative of gastric refluxate. In some embodiment, the method includes detecting at least one local condition, selecting a stimulation magnitude in accordance to the local condition, and stimulating a tissue in direct contact with and/or adjacent to the at least one of the terminals with the stimulation magnitude.

In an aspect of some embodiments a method of initiating muscle movement in at least a portion of the lower gastrointestinal tract comprises guiding a naso-intestinal tube having an electrode into a patient at least until a portion of the naso-intestinal tube extends into the patient's duodenum. The electrode may be electrically connected to a signal generator. A signal sequence may be generated such that the electrode stimulates a muscle contraction within a portion of the patient's lower gastrointestinal tract. The electrode may be positioned within the patient's duodenum or jejunum. In some embodiments, the electrode is positioned within the patient's esophagus. A method may include transmitting a signal sequence to the electrode to induce a muscle contraction in the patient's large intestine. A method may include generating a signal sequence at the electrode to stimulate a distally traveling wave of muscle contractions. The distally traveling wave may include peristalsis. A method may include generating a signal sequence at a plurality of electrodes to evoke at least two contractions at different locations in the lower gastrointestinal tract. The different locations in the lower gastrointestinal tract may include adjacent locations in the patient's small intestine. Different locations in the lower gastrointestinal tract may include remote locations in the patient's small intestine. Different locations in the lower gastrointestinal tract may include remote locations in the patient's small intestine and large intestine. A method may include generating at least two evoked contractions that are sequentially and/or timely generated according to a preset sequence.

In an aspect of some embodiments a method for initiating muscle movement in at least a portion of the lower gastrointestinal tract comprises positioning a GI contraction-stimulation system comprising an elongated tube having an electrode pair positioned within an esophagus, electrically connecting a first electrode of the electrode pair to a signal generator, electrically connecting a second electrode of the electrode pair to a grounding site, and powering on the GI contraction-stimulation system. The powering on the GI contraction-stimulation system may cause the system to generate a signal sequence at the electrode pair to evoke a muscle contraction within at least a portion of the patient's lower gastrointestinal tract. The powering on the GI contraction-stimulation system may cause the GI contraction-stimulation system to detect a change in impedance between the first electrode and the second electrode. The GI contraction-stimulation system may wait to generate a signal sequence at the electrode pair at least until the detected impedance exceeds a threshold value.

In an aspect of some embodiments a method for evoking motility in a GI tract portion comprises positioning a plurality of electrodes within an esophageal length. The esophageal length may be between a UES and an LES. The method may include transmitting a first signal to a first electrode, transmitting a second signal to a second electrode distal to the first electrode after transmitting the first signal, where the signals are configured to evoke motility in a GI tract portion located distally to the LES. In method may further include transmitting a third signal to a third electrode distal to the second electrode after transmitting the third signal. In some aspects, the method includes identifying a patient in need of lower GI tract motility. In some aspects, the method includes monitoring a patient's lower GI tract motility and/or stopping transmitting signals when lower GI tract motility is substantially restored. Signals may be transmitted over a time period of at least 15 minutes.

In an aspect of some embodiments, a system for stimulating muscle contractions within the large intestine may comprise a tubular member sized and configured to extend through a patient's mouth or nose to at least the patient's duodenum. An electrode may be mounted or mountable on the tubular member. The electrode may be configured to be and/or positioned to apply an electrical pulse to a portion of the patient's small intestine to evoke a muscle contraction. A generator may be configured to electrically connect to the electrode. The electrodes may be configured and positioned to apply an electrical pulse to a portion of the patient's stomach and/or esophagus. The generator may be sized and configured for prolonged intra-oral or intra-esophageal placement. The generator may comprise a pulse generator. The system may include a power source and the power source may be sized and configured for prolonged intra-oral or intra-esophageal placement. The tubular member may be feeding tube. The system may also include a plurality of electrodes spaced along a length of the tubular member. A distance of less than 5 cm may exists between at least two of the plurality of electrodes, and wherein a distance greater than 10 cm exists between a most proximal electrode and a most distal electrode. An array of switches may be coupled to the plurality of electrodes. The plurality of electrodes may be selectively connected electrically to a signal generator and/or connected electrically to a grounding site and/or disconnected. A plurality of electrodes may be arranged into a plurality of terminals. Each of the plurality of terminals may comprise 2 or 3 electrodes. The plurality of terminals may have one positive electrode and one negative electrode. The plurality of terminals may comprise two negative electrodes and one positive electrode, with the one positive electrode positioned between the two negative electrodes. The plurality of terminals may be positioned such that an intra-terminal distance between each electrode within a terminal is shorter than an inter-terminal distance between each of the plurality of terminals.

In an aspect of some embodiments a system for evoking motility in a gastrointestinal organ comprises a delivery member extendable and implantable in an esophagus above an LES, at least one electrode provided on the periphery of the delivery member, connected or connectable to an electrical signal generator such that a signal generated by the generator can cause an electrical stimulation to an esophageal muscle tissue in contact with said at least one electrode, and a controller comprising a processor and a memory. The memory may include preset commands for activating said generator to generate an activating session comprising a plurality of signal sequences for a duration of at least 15 minutes, thereby evoking motility in a target GI tract portion located distally to the LES. The activating session may include a sequence intermission between each two adjacent signal sequences. The sequence intermission may be between 0.5 minute and 5 minutes, optionally between 1 minute and 2 minutes.

In an aspect of some embodiments a method for evoking motility in a gastrointestinal organ comprises stimulating at least two portions of a patient's esophagus between the LES and the UES. The stimulations may comprise a plurality of signal sequences applied for a duration of at least 15 minutes thereby evoking motility in a target GI tract portion located distally to the LES. The method may include rest periods in between stimulation periods.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of various embodiments. In this regard, the description taken with the drawings makes apparent to those skilled in the art how embodiments of the invention may be practiced. In the drawings:

FIGS. 2A-C schematically illustrate a partial cut view of a contractions wave stimulating system provided in an esophagus, shown at different operation stages, in accordance with some embodiments of the present invention;

FIGS. 3A-D schematically illustrate a first exemplary stimulation sequence and a correspondingly generated patterned esophageal motion, in accordance with some embodiments of the present invention;

FIGS. 4A-D schematically illustrate a second exemplary stimulation sequence and a correspondingly generated patterned esophageal motion, in accordance with some embodiments of the present invention;

DETAILED DESCRIPTION OF CERTAIN EMBODIMENTS

Figure 1A:
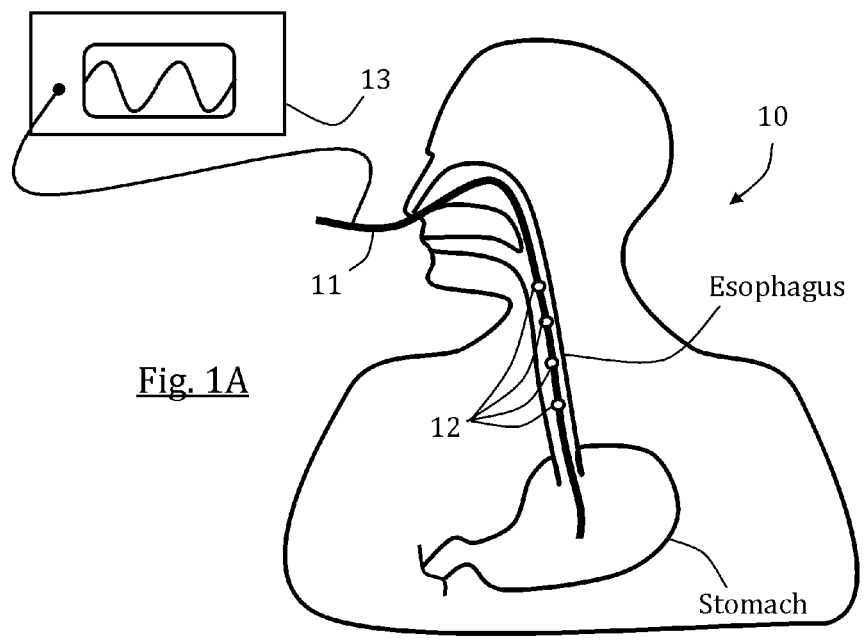
FIG. 1A schematically illustrates an exemplary nasogastric tube positioned in a patient's esophagus and including a plurality of stimulators, in accordance with an embodiment of the present invention.

The following preferred embodiments may be described in the context of exemplary esophageal stimulation procedures for ease of description and understanding. The term "exemplary" used throughout this description means "serving as an example, instance, or illustration," and should not necessarily be construed as preferred or advantageous over other embodiments. Other embodiments may be utilized and the described devices and methods may be adapted for other clinical applications without departing from the spirit or scope of the subject matter presented here.

The present invention, in some embodiments thereof, relates to devices and methods for initiating and/or sustaining minimal function of at least a portion of the GI tract, and in particular to devices and methods for generating movement in one or more GI organs, optionally including at least esophageal motility for diminishing retrograde flow of gastric contents and/or for promoting gastric digestion. Devices and related methods described herein may be used for stimulating any GI organ, such as but not limited to, the: esophagus, gullet, stomach wall, pylorus, duodenum, jejunum, ileum, small intestine, caecum, colon, rectum, and large intestine.

International patent application No. PCT/IB2012/001546, the disclosure of which is fully incorporated herein by reference, relates to devices and methods for evoking esophageal motion, optionally including a distally advancing contractions wave, optionally though not necessarily including peristalsis, optionally for diminishing retrograde flow of gastric contents.

Similar esophageal motion may promote motility in other regions of GI tract as well, which may be useful for other purposes such as improved gastric digestion including emptying. A proper gastric digestion includes occasional contractions of stomach and intestine portions. Patients in intensive care and/or otherwise anesthetized, or post-operative patients, may have a substantial drop in digestion related function which may result in insufficient stomach emptying to the intestine. By stimulating portions of the esophagus, contractive phenomena may be aroused as well in other portions such as in the stomach and/or areas in the intestines. The present inventions disclosed herein are at least partially based on the unexpected and surprising result that a patient's lower digestive system can be stimulated and/or "awakened" by stimulation of the patient's esophagus. Additionally, multiple organs within the lower GI tract may be awakened at about the same time. Thus, a patient's digestive system function may be at least partially restored in areas distal to the LES by stimulation of the esophagus alone. Not all esophageal stimulations to stimulation of organs distal to the LES. However, when the system disclosed herein simulates multiple points of a patient's esophagus over a relatively long period of time, one or more organs distal to the LES, which are not directly stimulated are also evoked to produce motility. For example, when at least four points of a patient's esophagus are stimulated to produce sequences of esophageal contractions for at least 15 minutes, in some cases at least 30 minutes, lower digestive function and/or peristalsis may return.

In some embodiments, the systems and methods disclosed herein use one or more electrodes positioned within an esophageal length in order to stimulate digestion in a region distal to the LES. In some embodiments, sending signals to at least two electrodes, in some cases to at least three electrodes or to at least four electrodes, of the same designated polarity, positioned in a patient's esophagus, and without any electrodes or other stimulating devices placed within other portions of the patient's digestive tract proximal to the LES, causes indirect evocation of the patient's digestive tract distal to the LES. The patient's esophagus may be stimulated for discrete time periods throughout the day. For example, the patient's esophagus may be stimulated for about 15 minutes, or for about 20 minutes, or for about 30 minutes. In some embodiments, the patient's esophagus is stimulated three times a day, for 30 about minutes each time. Such stimulations can promote motility in locations distal to the LES.

An aspect of some embodiments relates to a system for generating a patterned esophageal motion. A patterned esophageal motion may be any local or cross-esophageal muscular expansion or contraction, or any combination thereof, evoked and/or orchestrated following generated stimulation. The pattern may be a chosen shape and/or magnitude of a local esophagus contraction and/or a distally progressive contractions wave having chosen characteristics, including but not limited to contraction force, wave travel velocity and wave occurrence frequency. In some embodiments, the patterned esophageal motion includes peristalsis, optionally simulating a naturally occurring esophageal peristalsis or creating a synthetic peristalsis based on an algorithmic sequence of stimulations, and/or any combination of local contractions, distally progressive contractions wave and/or selectively evoked naturally occurring peristalsis at a patient's esophagus.

In some embodiments, the system includes at least one stimulator adapted to stimulate a portion of the esophagus to evoke a shaped contractive reaction. In some embodiments, the at least one stimulator includes an electrode configured for electrical stimulation of adjacent/contacting esophagus muscle tissue. A stimulating electrode may be connectable or provided readily connected with a generator, optionally a pulse generator, configured to generate a chosen sequence of stimulations. Optionally, alternatively or additionally, an internal power and/or signal source may be provided with the system that is sized and configured for intra-body (e.g., intra-orally) placement, optionally in or adjacent the esophagus. In some other optional embodiments, a power and/or signal source may be provided (e.g., worn) on the patient. In some exemplary embodiments, at least one electrode and/or sensor is connected with such an internal power source sized and configured for placement on a medical intubation device (e.g., a feeding tube or other elongated tube, which extends through a patient's nose or mouth into at least the esophagus, and optionally, through the esophagus into the stomach or small intestine).

In some embodiments, the system further includes one or more safety features to ensure that electrical stimulations are only applied to the electrodes of the esophageal tube when all electrodes are positioned within a patient. Such a system may help ensure that electrical pulses are not applied when any of the electrodes are positioned external to a patient, for example, during insertion, removal, or adjustment of the tube. In some embodiments, the system has a power switch or button, which prevents current from traveling from the power supply to the electrodes unless powered on. Additionally, some embodiments have a backup safety feature to reduce risk of shock or injury in the event the tube is removed from the patient before powering down. In some such embodiments, when the system is powered on, it is configured to detect the resistance across one or more electrode pairs of the esophageal tube. In some embodiments, the system detects the resistance across the proximal-most pair of electrodes. When the resistance is above a certain threshold, no stimulation pulses will be provided to the electrodes. When the resistance falls below the threshold, the system will activate and pulse sequences can be provided to one or more of the electrodes. In some embodiments, the threshold is set near the resistance value typically detected across the electrodes when positioned within the esophagus or nasal cavity.

In some embodiments, the backup safety feature is embodied directly in hardware. The safety feature of some embodiments is controlled by a Digital Signal Processor ("DSP"), an Application Specific Integrated Circuit ("ASIC"), a Field Programmable Gate Array ("FPGA") or other programmable logic device, discrete gate or transistor logic, discrete hardware components, or any combination thereof designed to perform the functions described herein. In some embodiments, the backup safety feature logic may be programmed into a general purpose processor, such as, for example, the processor within the system's signal generator. A general purpose processor may be a microprocessor, but in the alternative, the processor may be any processor, controller, microcontroller, or state machine. If implemented in software, the backup safety feature and other functions disclosed herein may be stored on, or transmitted over as, one or more instructions or code on a tangible, non-transitory computer-readable medium. In some embodiments, the system includes a plurality of stimulators provided at different relative locations within the esophagus, optionally also in other GI tract anatomical locations.

A local contraction of the esophagus, or any combination or pattern of esophageal contractions may increase local and/or average esophageal pressure. Optionally, alternatively or additionally, stimulation is used to decrease local and/or average volume entrapped along the esophagus lumen between the LES and the UES, optionally also elsewhere along the GI tract, thereby increasing local and/or average pressure. By increasing the pressure at a local segment of the esophagus lumen, for example, a retrograded material or chyme if present may be forced to travel backward to a distal lumen segment being less pressured, whereas by increasing the average or overall pressure in the esophagus, a possible reflux causing positive pressure difference between the stomach and the esophagus may be diminished and even reversed, thereby diminishing the possibility or volume of refluxed material or even preventing reflux. In some embodiments, a local and/or average pressure caused by a single evoked contraction or a series of evoked contractions may be equal or higher than 15 mmHg, optionally equal or higher than 25 mmHg, optionally equal or higher than 50 mmHg, and optionally equal or higher than 100 mmHg, or lower, higher, or intermediate to any of said values.

Optionally, alternatively or additionally, generating local and/or patterned contraction(s) in the esophagus also evoke motility in other GI tract anatomic locations such as in the small intestine, colon, rectum and/or others. Such evoked motility, especially if emerged in a dysfunctional, temporarily or permanently, GI tract portion, may revive at least partially a GI function such as gastric digestion and/or emptying.

In some embodiments, the system further includes, is provided with, or is connected to a medical intubation device that is sized and configured for nasal or oral placement in a patient's esophagus. In some embodiments, the medical intubation device is a gastric feeding tube such as a nasogastric or a nasojejunal intubation.

In some embodiments, at least one stimulator is fixed to the medical intubation device. Optionally, alternatively or additionally, at least one stimulator is provided with a fixator configured for fixedly covering a portion of the medical intubation device.

In some embodiments, the at least one stimulator includes at least two stimulators sequentially positioned along an esophageal length, each stimulator being configured to stimulate a different esophageal portion. Optionally, a plurality of stimulators is provided along the effective length of the medical intubation device. Optionally, an effective length may be configured for positioning in a defined segment of the esophagus; while alternatively, an effective length may be configured to include at least a segment along esophagus and at least another segment in a distinct GI organ, optionally the intestines, either continuously to the esophagus segment or discretely thereto.

In some embodiments wherein the at least one stimulator comprises a plurality of electrodes, the electrodes are arranged in groups referred to herein as terminals. In some embodiments, two electrodes (i.e., "electrodes pairs") or more form a terminal. In some such embodiments, one electrode is a positive electrode, which receives current from a signal generator, and the other electrode is a negative electrode, which is grounded. The distance between each terminal may be fixed or variable, and the terminals are spaced such that the distance between each terminal is greater than the distance between each electrode within any given terminal. For example, the width of the terminal (i.e., the distance between the electrodes of a terminal) may be 5-10 mm, and optionally 8 mm. The distance between each terminal may be 15-30 mm, optionally 20 mm, or optionally, below, above, or intermediate to said values. Optionally, additionally, or alternatively, at least some electrodes are arranged in same distance therebetween so that a width of a terminal equals the distance between each terminal. In some such embodiments, the distance between each adjacent electrodes/terminals is at least 5 mm, optionally at least 10 mm, optionally at least 20 mm, optionally at least 30 mm, or higher, or lower, or intermediate value. In other embodiments having two electrodes per terminal, the system also comprises an array of controlled relays coupled to the electrodes. The array of controlled relays may be configured to selectively transition each electrode between a positively connected state, a grounded state, and a disconnected state. In still other embodiments, three electrodes form a terminal. In such embodiments, two of the electrodes may be grounded, and the third electrode, which is positioned between the two grounded electrodes, may be a positive electrode connected to a signal generator. The electrodes are positioned such that the positive electrode will close a circuit with the two negative (grounded) electrodes of the same terminal Such a design may position the center of stimulation at the location of the positive electrode.

In some embodiments, the system includes at least one sensor. Optionally, the sensor is provided on the medical intubation device distally to the at least one stimulator. Optionally, the sensor is a pH sensor, optionally adapted to sense a change (e.g., decrease) of local pH, for example due to the presence of gastric contents proximally to the LES. Optionally, alternatively or additionally, an impedance sensor may be used, configured for sensing a change in impedance of tissues provided between stimulators and/or electrodes, optionally correlative to a reaction to gastric contents or other substances. Optionally, alternatively or additionally, other sensor types may be used, including but not limited to a pressure sensor, a manometer, a moisture sensor, a temperature sensor, a motion sensor, a capacitance sensor and a mechanical sensor.

In an aspect of some other embodiments, there is provided a method for generating esophageal peristalsis in a patient intubated with a gastric tube, and/or for generating motility in other GI tract organs. In some embodiments, the method comprises at least one of the following steps, optionally with no particular order:
1. positioning at least two electrodes, including one or more proximally positioned electrodes and one or more distally positioned electrodes, at spaced positions along the gastric tube, where the positions are selected such that after installation of the gastric tube, the at least two electrodes will be between the upper esophageal sphincter (UES) and the lower esophageal sphincter (LES);
2. electrically connecting the at least two electrodes to a generator; and/or
3. generating a signal sequence including a first signal at the proximally positioned electrode thereby stimulating a proximal esophageal tissue and a second signal at the distally positioned electrode thereby stimulating a distal esophageal tissue.

In some embodiments, the electrodes apply electrical current in a series of one or more electrical trains, wherein each train is composed of a series of cycles, and each cycle includes one pulse. Each electrical pulse has an amplitude; in preferred embodiments, the amplitude is higher than a stimulating threshold. In some embodiments, the stimulating threshold is between 5V and 20V, optionally between 8V and 10V or between 10V and 15V; in other embodiments, the stimulating threshold may be higher or lower than said values. Each pulse is provided for a duration of time. In some embodiments, the pulse width (i.e., the duration) is equal to or greater than 5 milliseconds, and optionally, equal to or greater than 10 milliseconds. The applied pulse is followed by a duration of lower current and/or no current. Together, one pulse and one duration of low current compose a cycle. In some embodiments, one cycle lasts 20 ms; in other embodiments, one cycle lasts 15 ms, or optionally 30 ms, or less than, greater than, or intermediate to said values. In some embodiments, multiple cycles are provided successively such that together the cycles form a train having a duration of one to two seconds. In other embodiments, trains are provided that are longer or shorter in duration. The train is then followed by a duration of no current or low current produced by below-threshold voltages.

In some embodiments, the sequence of trains or other signal sequence produces a wave of contractions (i.e., distally progressing esophageal contractions) that travels a length along the esophagus. In some embodiments, the contractions generate or simulate natural peristalsis. In some embodiments, a contractions wave in the esophagus initiates at least minimal functionality in one or more other portions of the GI tract. In some such embodiments, contractions continue to travel as a wave distally through the stomach and through at least a portion of the small intestine. In some embodiments, the wave of contractions evokes activity in the large intestine. In other embodiments, the contraction wave in the esophagus induces remote contractions in the lower GI tract, such as, for example, contractions within the duodenum, jejunum, ileum, caecum, colon, and/or rectum.

In some embodiments, before each train or pulse, one or more below-threshold pulses are applied to the tissue to prime the tissue and induce it to contract more firmly and efficiently and to begin contracting at lower voltage stimulation levels. Optionally, a preliminary, below-threshold train is applied before each stimulating train or pulse. In some embodiments, a continuous below-threshold train is applied to specific portions of the esophagus to desensitize, and thereby avoid unneeded contractions within, said portions. For example, the LES must be open in order for material to pass from the esophagus into the stomach. In one embodiment therefore, one or more electrodes may also be positioned on the gastric tube such that after installation they are adjacent the LES to provide a continuous below-threshold train which will be applied to the LES to desensitize it so that it does not contract when material arrives. Such electrode(s) may also be used to close the LES if that is a desired response under some circumstances.

Referring now to the drawings, FIG. 1A schematically illustrates an exemplary system 10 comprising an elongated member 11 positioned in a patient's esophagus and including a plurality of stimulators 12, in accordance with an embodiment. Elongated member 11 may be any plastic or elastic rod or tube sized to enter and be pushed through the esophagus, preferably with no injury to adjacent tissues. Elongated member may be a probe, a catheter and/or a nasogastric tube (NGT); the latter is optionally used for injecting food directly to a patient's stomach and/or pumping out chyme to relieve excessive gastric pressure. Stimulators 12 may be any mechanical, electrical or chemical local muscle or neural stimulators. Four stimulators 12 are shown for illustrative purposes, although any other number of stimulators may be provided. In some exemplary embodiments, stimulators 12 are or include at least one electrode. In some embodiments, each shown stimulator 12 represents a number of electrodes (e.g., a terminal), optionally provided around a local periphery of elongated member 11. In some embodiments, stimulators 12 are provided in a sequential order, optionally having a constant or selectively changeable distance therebetween. Optionally, stimulators 12 comprise bi-polar electrodes so that pairs of adjacent non-short-circuited electrodes can be used for closing an electrical circuit and thereby stimulate an esophageal muscle tissue in-contact and in-between the two electrodes. A generator 13, optionally an electrical signal generator, is shown connected to stimulators 12 via elongated member 11, optionally over and along its outer periphery or via a lumen thereof. To produce a series of esophageal contractions in accordance with a chosen scheme or logic, such as optionally simulating a naturally occurring esophageal peristalsis, separate generator outputs may be provided to separate electrodes or electrode groups 12. In some advantageous embodiments, the spacing between electrodes or electrode groups 12 is less than 5 cm, and the distance between the most proximal electrode or electrode group 12 and most distal electrode or electrode group 12 is at least 10 cm. This allows sequential stimulation of the electrodes or electrode groups 12 along a significant portion of the esophagus between the UES and the LES.

Figure 1B:
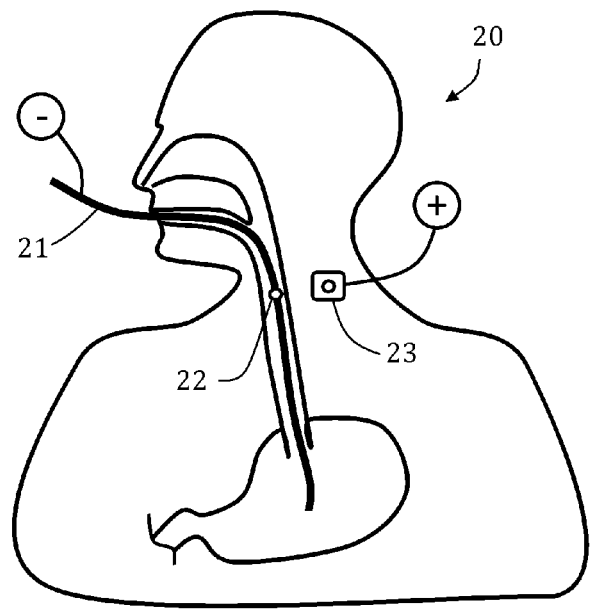
FIG. 1B schematically illustrates an exemplary oral feeding tube positioned in a patient's esophagus and including a mono-polar stimulator, in accordance with an embodiment of the present invention.

In FIG. 1B, an exemplary system 20 is schematically illustrated comprising an oral feeding tube 21 positioned in a patient's esophagus and including a mono-polar stimulator 22, in accordance with an embodiment. Although it is commonly more safe and convenient to place an esophageal intubation via a nasal cavity, there might be circumstances (e.g., with infant patients) where a tube is inserted via the oral cavity as suggested in this figure. Mono-polar stimulator 22 is electrically connected to an outside source or ground (shown in the figure as "(−)") and is selectively capable of closing an electrical circuit with an external electrode 23, optionally positioned on the patient's neck skin. A single electrode may be used to stimulate a neutrally sensitive region thereby evoking an esophageal contraction wave from the stimulated region and downward, optionally to the LES or the stomach interim. Optionally, alternatively or additionally, a single electrode may be used for local muscle contraction in order to serve as a barrier for refluxed gastric contents and/or for decreasing overall esophagus volume and increasing esophageal pressure, and/or optionally evoking motility in other GI tract organs.

Figure 1C:
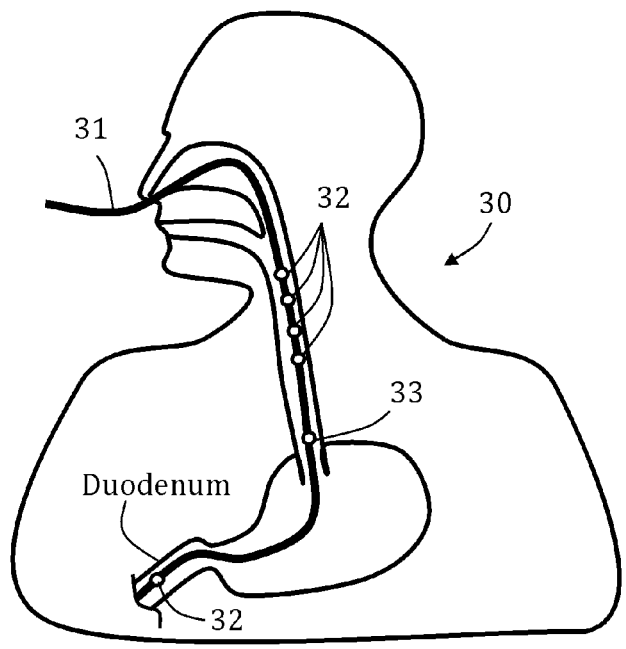
FIG. 1C schematically illustrates an exemplary feeding tube positioned in a patient's esophagus and extending into the patient's small intestine, the feeding tube including a plurality of stimulators and a sensor, in accordance with an embodiment of the present invention.

In FIG. 1C, an exemplary system 30 is schematically illustrated comprising a feeding tube 31 positioned in a patient's esophagus and including a plurality of stimulators 32 and a sensor 33, in accordance with an embodiment. Feeding tube 31 may be used to introduce partly digested food or fluids directly to the small intestine (e.g., opened at the duodenum or at the jejunum). In some embodiments, the stimulators 32 are positioned on the feeding tube 31 such that, when the feeding tube 31 is in place within a patient, the stimulators 32 are located within the esophagus, the stomach, the small intestine, or any combination thereof. For example, in FIG. 1C, the stimulators 32 are positioned in the esophagus and the duodenum of the small intestine. In some embodiments, stimulators are positioned regularly along the length of the feeding tube 31. For example, in one embodiment, a stimulator or stimulator pair is positioned every 4 cm along the feeding tube 31, allowing for multi-location stimulation within multiple GI organs.

Sensor 33 of FIG. 1C may be a pH sensor, optionally positioned adjacent or proximal to the LES or stomach entry. In the case of a substantially low pH, such as in the presence of acid refluxed chyme, sensor 33 automatically signals and/or initiates the stimulations protocol for electrodes 32 to force the gastric content to flow back towards the stomach. In cases where no sensor is present, different stimulation protocols may apply, for example continuous stimulation regimes in which different electrodes are used sequentially to stimulate local tissues at specific frequencies and magnitudes. Optionally, alternatively or additionally, a local esophageal contraction or spasm is evoked, for any chosen duration, to act as a local physical barrier, thereby preventing or diminishing refluxed substance from passing therethrough. Such a local contraction/spasm may be singular or generated at different occasions and/or portions of the esophagus. Optionally, alternatively or additionally, at least one of the electrodes may be applied as sensors, for example bio-impedance sensors.

Figure 1D:
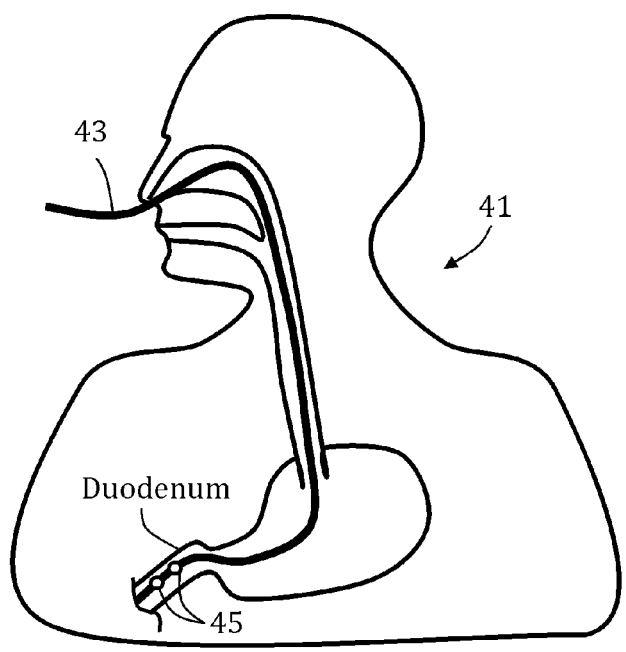
FIG. 1D schematically illustrates an exemplary feeding tube positioned in a patient's esophagus and extending into the patient's small intestine, the feeding tube including a plurality of stimulators, in accordance with an embodiment of the present invention.
Figure 3B:
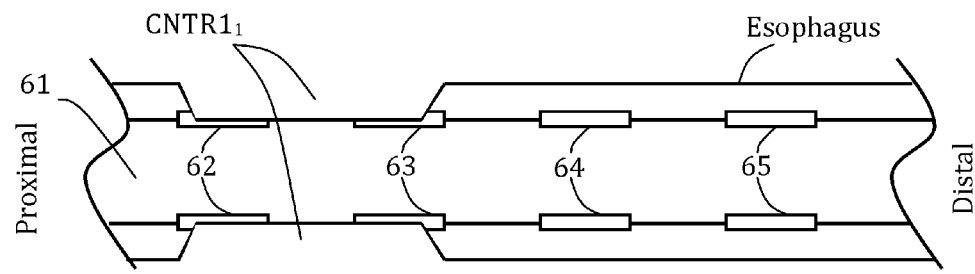
Figure 3C:
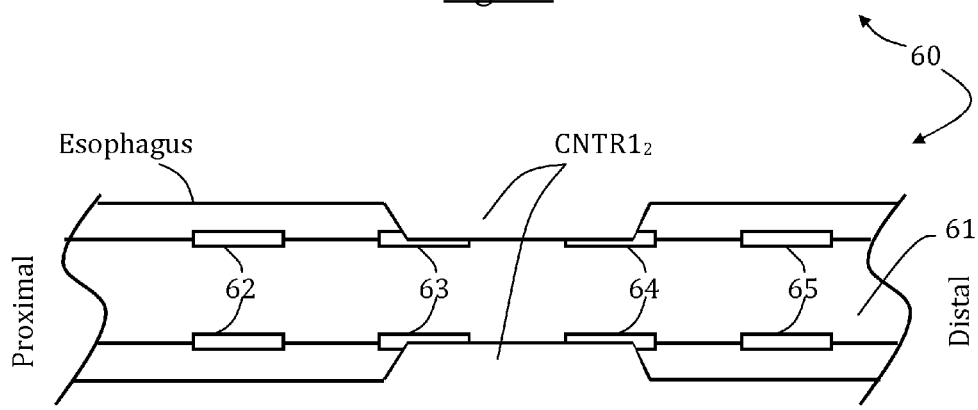
Figure 3D:
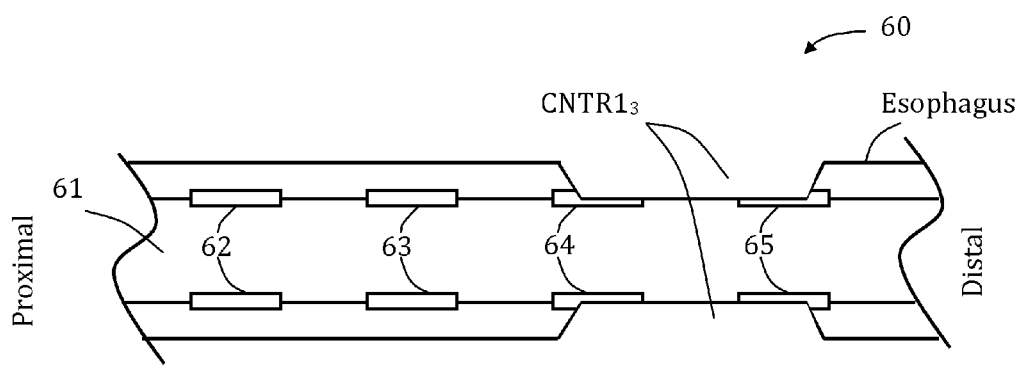
Figure 4B:
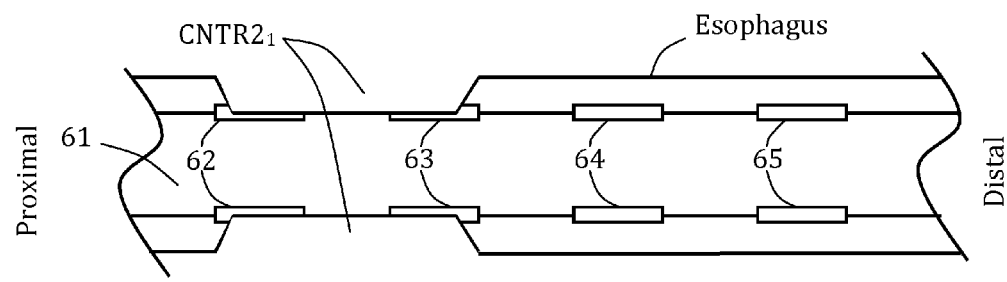
Figure 4C:
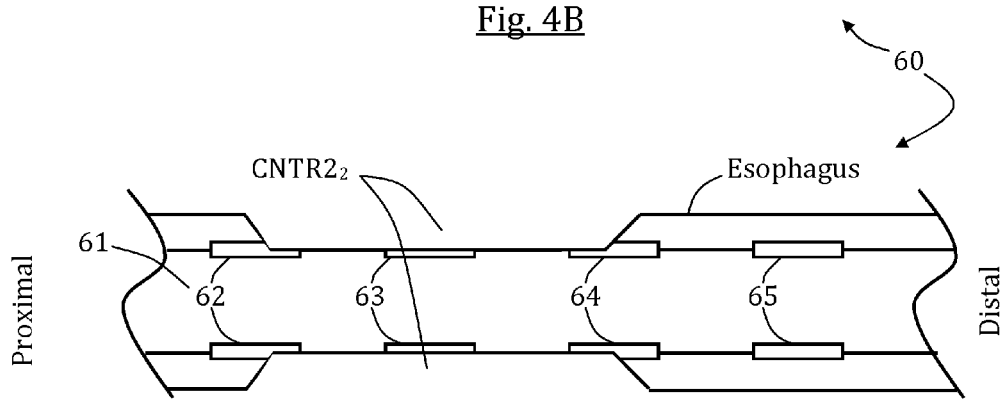
Figure 4D:
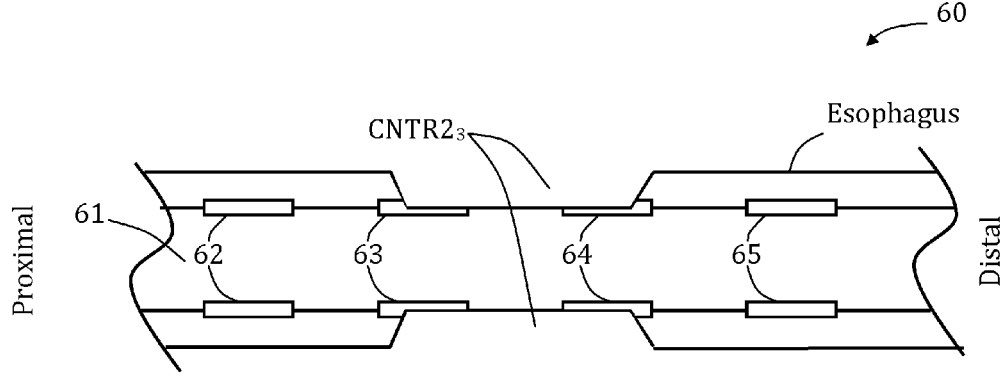
Figure 5A:
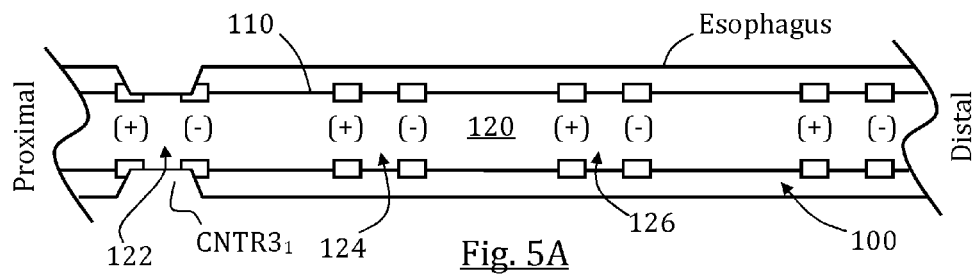
FIGS. 5A-D schematically illustrate a third exemplary stimulation sequence and a correspondingly generated patterned esophageal motion, in accordance with some embodiments of the present invention.
Figure 5B:
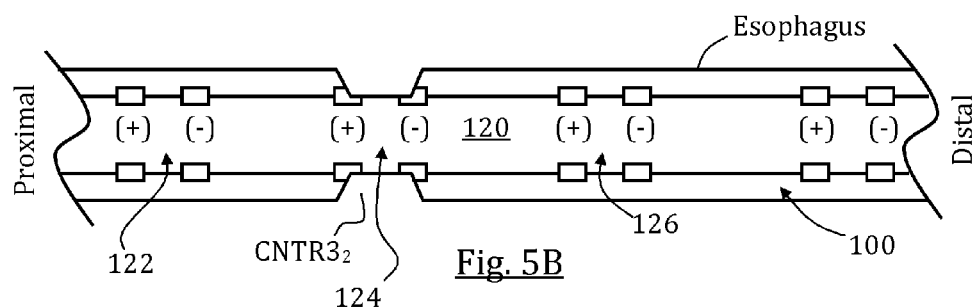
Figure 5C:
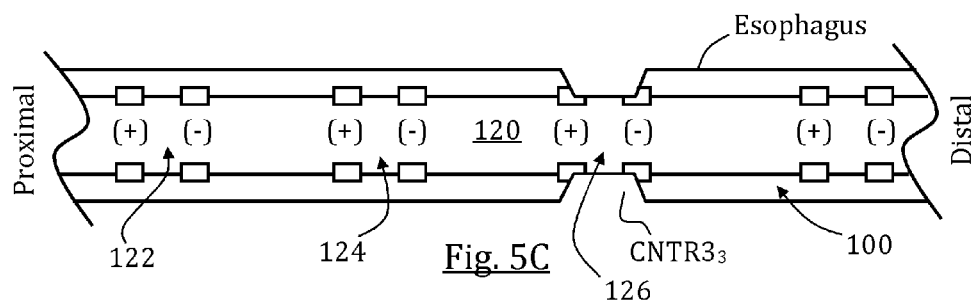
Figure 5D:
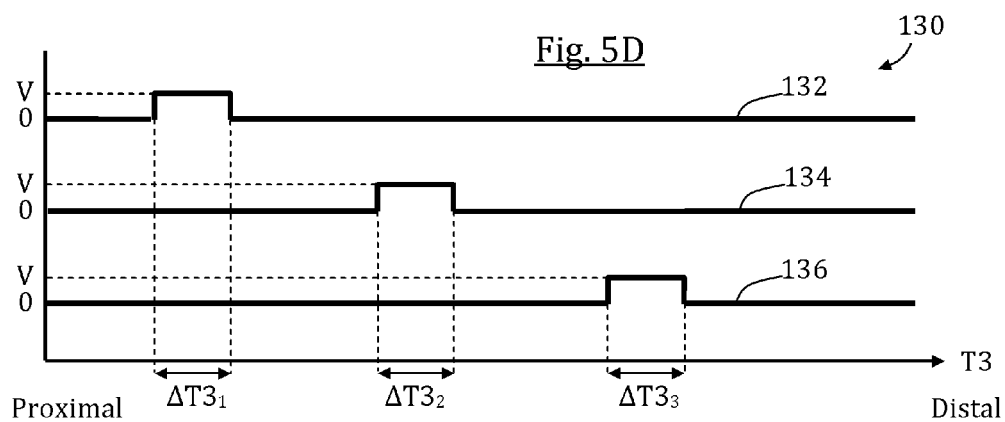

FIG. 1D schematically depicts an exemplary system 41 comprising a naso-intestinal (e.g., naso-jejunal) tube 43 positioned through a patient's nose and esophagus and extending into the small intestine. The naso-intestinal tube 43 of FIG. 1D is a feeding tube designed to deliver liquid foods, or other food or nutrients directly into the small intestine. A plurality of electrodes 45 are positioned in or on a portion of the naso-intestinal tube 43 within the small intestine and are fixedly or removably secured to the naso-intestinal tube 43. Various stimulation protocols may be applied to the electrodes 45 to facilitate motility in the lower GI tract. In some embodiments, applied stimulation protocols stimulate local tissues within the duodenum and/or jejunum. In some embodiments, localized contractions within the small intestine induce one or more contractions in the large intestine. In other embodiments, the applied stimulation protocols generate one or more waves of contractions, which move distally through the small intestine, and optionally, through all or part of the large intestine. In some embodiments, the contractions wave simulates naturally occurring peristalsis.

Reference is now made to FIGS. 2A-C which schematically illustrate a partial cut view of a contractions wave stimulating system 35 provided in an esophagus, shown at different operation stages, in accordance with some embodiments. As shown in FIG. 2A, in one embodiment, a gastric content or chyme travels proximally away from the stomach adjacent to a pH sensor 36 previously deployed in the esophagus. Once a pH change is sensed, proximally positioned stimulators 38 initiate a stimulation having a magnitude and/or frequency adapted to evoke a distally advancing esophageal contractions wave capable of pushing back the chyme. As shown in FIGS. 2B and 2C, a contractions wave CW is created by adjacent stimulators 38 and moves distally while pushing the chyme back towards the stomach. Optionally, CW simulates a naturally occurring esophageal peristalsis, although the motion may be different from natural peristalsis in at least one factor, for example, in magnitude, speed and/or frequency.

Reference is now made to FIGS. 3A-D which schematically illustrate a first exemplary stimulation sequence 40 and a correspondingly generated patterned esophageal motion, using a stimulation system 60, in accordance with some embodiments. As shown, system 60 includes a catheter 61 extending across a length in the esophagus and a plurality of bi-polar stimulation electrode pairs, including a proximal-most electrode 62, then electrode 63, electrode 64 and electrode 65. In this embodiment, each electrode encircles the catheter. Stimulation sequence or protocol 40 generates a combination of signals through different channels, including a channel 42 adapted to stimulate an esophageal muscle tissue provided between electrodes 62 and 63, a channel 44 adapted to stimulate an esophageal muscle tissue provided between electrodes 63 and 64, and a channel 46 adapted to stimulate an esophageal muscle tissue provided between electrodes 64 and 65. As shown, channel 42 stimulates the esophagus with voltage V at duration $\Delta T1_1$ thus evoking a local contraction $CNTR1_1$ at the same duration Immediately following, channel 44 stimulates the esophagus with voltage V at duration $\Delta T1_2$ thus evoking a second local contraction $CNTR1_2$ at the same duration. This is followed by stimulation through channel 46 with voltage V at duration $\Delta T1_3$, which evokes a third local contraction $CNTR1_3$ at the same duration.

FIGS. 4A-D schematically illustrate a second exemplary stimulation sequence 50 and a correspondingly generated patterned esophageal motion, still using stimulation system 60, in accordance with some embodiments. This time two channels, 52 and 54, are shown with corresponding stimulation durations $\Delta T2_1$ and $\Delta T2_3$ that are overlapping at partial duration $\Delta T2_2$. This way, a traveling contractions wave simulates a general peristaltic motion in which a first local contraction $CNTR2_1$ extends distally to become $CNTR2_2$ and only afterwards diminishes to leave a distal local contraction $CNTR2_3$.

FIGS. 5A-D schematically illustrate a third exemplary stimulation sequence 130 and a correspondingly generated patterned esophageal motion using a system 100 for evoking motility in a GI tract portion, in accordance with some embodiments. As shown, system 100 includes an elongated member 110 (e.g., a tubular portion such as of a feeding tube) extending across a length in the esophagus, and a series of electrodes 120 arranged as a plurality of bi-polar stimulation electrode pairs, including a proximal-most electrodes pair 122, then electrodes pair 124, and electrodes pair 126. In some embodiments, the distance between each electrode in an electrodes pair (i.e., a "pair length" or a "terminal width") is similar or same to the distance between each adjacent electrodes pairs such that all electrodes 120 are substantially evenly spaced. In some such embodiments, the distance between each adjacent electrodes is at least 5 mm, optionally at least 10 mm, optionally at least 20 mm, optionally at least 30 mm, optionally at least 50 mm. In this embodiment, each electrode encircles the catheter. Optionally and alternatively, the length of each electrodes pair is substantially different (optionally shorter) than the distance between each adjacent electrodes pairs. In some such embodiments, the length of each electrodes pair is at most 5 mm, optionally at most 10 mm, optionally at most 20 mm, whereas the distance between each adjacent electrodes pairs is at least 10 mm, optionally at least 20 mm, optionally at least 30 mm, respectively.

Stimulation sequence or protocol 130 generates a combination of signals through different channels, including a channel 132 adapted to stimulate an esophageal muscle tissue provided between electrodes pair 122, a channel 134 adapted to stimulate an esophageal muscle tissue provided between electrodes pair 124, and a channel 136 adapted to stimulate an esophageal muscle tissue provided between electrodes pair 126. As shown, channel 132 stimulates a first esophagus portion with voltage V at duration $\Delta T3_1$ thus evoking a local contraction $CNTR3_1$. A first period afterwards, channel 134 stimulates a second esophagus portion with voltage V at duration $\Delta T3_2$ thus evoking a second local contraction $CNTR3_2$. A second period afterwards, channel 136 stimulates a third esophagus portion with voltage V at duration $\Delta T3_3$, which evokes a third local contraction $CNTR3_3$. In some embodiments, at least one of said first period and said second period is between 0.1 second and 2 second, optionally equal or less than 0.5 second.

Figure 6A:
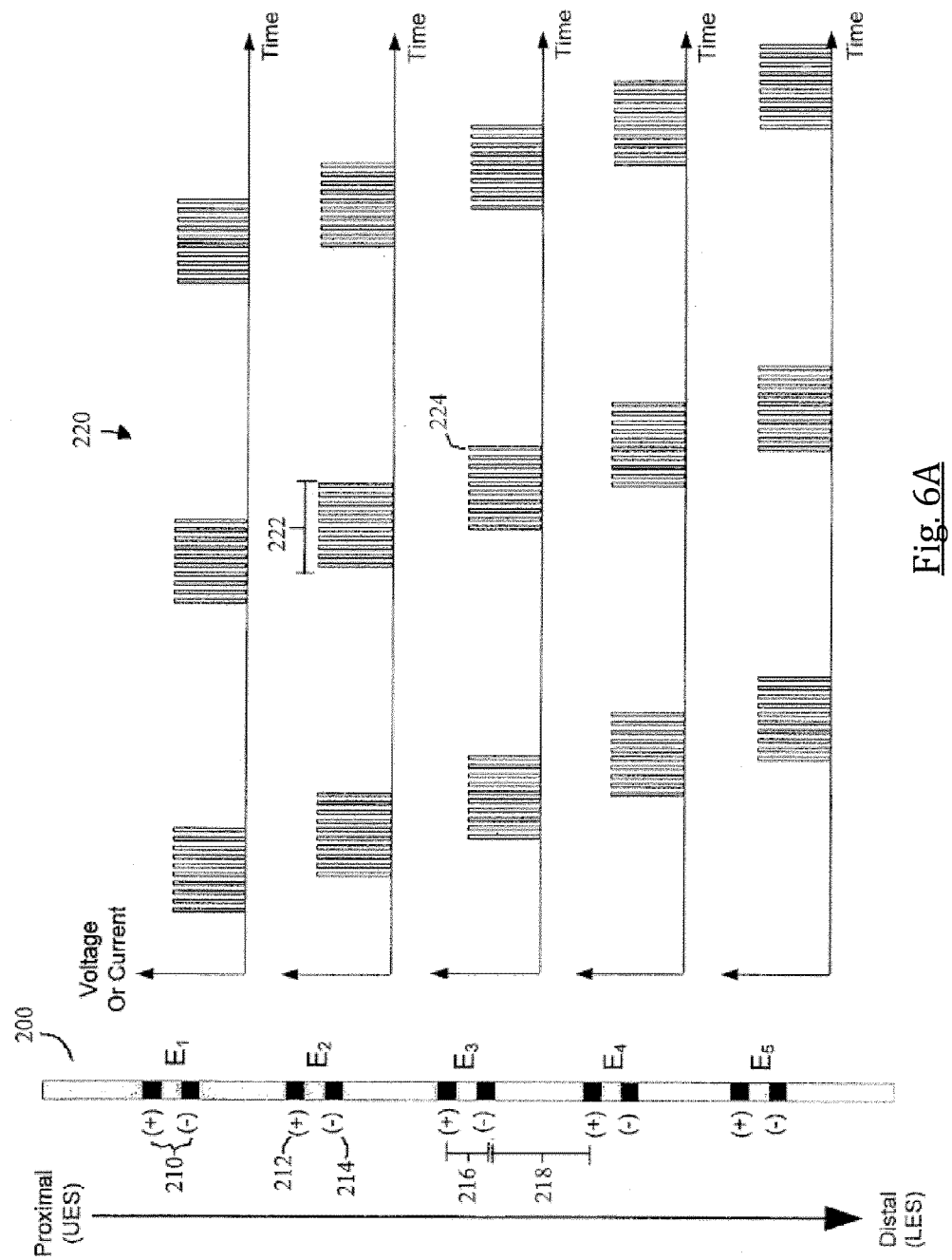
FIG. 6A schematically illustrates a top view of an exemplary esophageal intubation tube provided with a plurality of terminals comprising two electrodes each; an exemplary signal sequence from each terminal is also illustrated, in accordance with some embodiments of the present invention.
Figure 6B:
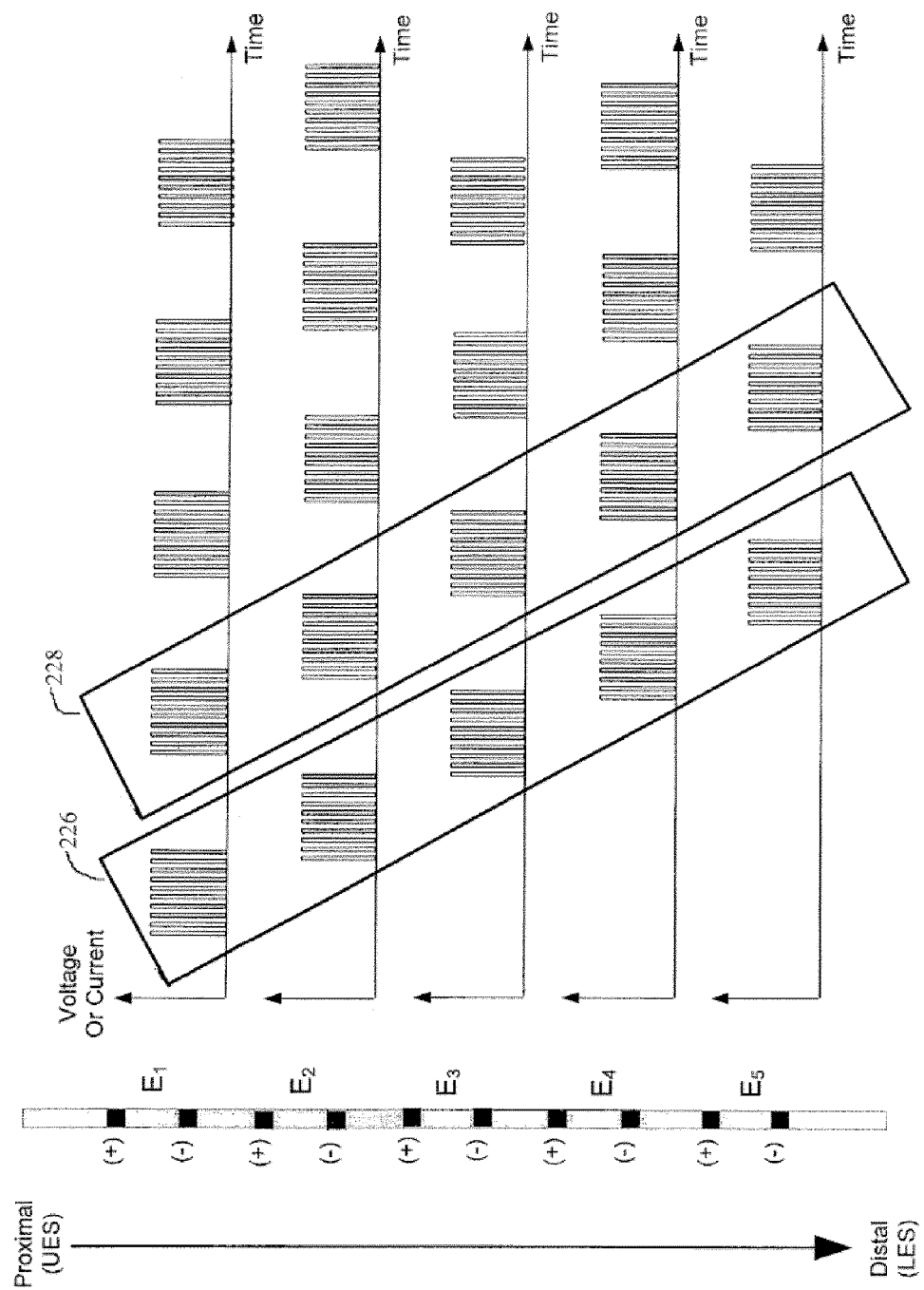
FIG. 6B schematically illustrates a top view of an exemplary esophageal intubation tube provided with a plurality of terminals comprising two electrodes each; an exemplary signal sequence from each terminal is also illustrated, in accordance with some embodiments of the present invention.

FIG. 6A schematically illustrates an exemplary esophageal intubation tube 200 provided with a plurality of terminals 210 comprising two electrodes each: a positive electrode 212 and a negative (grounded) electrode 214, in accordance with some embodiments. The electrodes are spaced such that the distance 218 between each terminal is greater than the distance 216 between each electrode within any given terminal. As used in this application, whenever a distance between electrodes is mentioned, the center to center distance is being referred to. The electrodes 212 and 214 of each terminal 210 are connected to a remote electrical signal generator via electrical circuitry (not shown). A current or voltage, optionally a pulsed current or voltage, is provided to the positive electrode 212. An exemplary signal sequence 220 is also illustrated in FIG. 6A. As shown, a train 222 of pulses 224 is provided to each terminal 210. In some embodiments, the signal sequence 220 is staggered in time such that distally-located terminals receive stimulating trains 222 after more proximally-located terminals. By providing a plurality of terminals 210 receiving staggered signal sequences, a wave of contractions, optionally simulating peristalsis, may be generated. In this example there are three "waves" of stimulations that progress down the esophagus and a second wave starts only after the first wave is finished (with no overlapping). A different approach is seen in FIG. 6B, where a second wave starting at the upper portion of the esophagus begins before a previous wave of stimulations down the esophagus is completed. In this implementation, there may be two distant esophagus portions which contract at the same time. This may increase overall peristalsis efficacy, while better overcoming still retrograding material that managed to "infiltrate" through distal contractions/waves.

In some intubation tube embodiments, such as for example, the esophageal intubation tube embodiment of FIG. 6B, the electrodes 252 are spaced uniformly along the length of the intubation tube 250. In some such embodiments, polarity alternates between each electrode 252, forming bipolar electrode pairs 254. For example, in FIG. 6B, there are five electrode pairs 254, and the distance between each electrode 252 within an electrode pair is equidistant to the distance between electrodes 252 of adjacent pairs.

In an additional embodiment of a stimulation protocol, as described with reference to the intubation tube 250 of FIG. 6B, stimulation originates in the proximal-most electrode pair $E_1$. Various stimulation sequences can be applied to the first electrode pair $E_1$. One embodiment of potential stimulation sequences is provided in the table below. In some embodiments, stimulation sequence #1 is applied first. If adequate stimulation is not achieved, sequence #2 is applied to the electrode pair $E_1$. Application of the various stimulation sequences progresses until adequate stimulation is achieved. In one such embodiment, adequate stimulation is defined as a localized contraction of 40 mmHg. In other embodiments, adequate stimulation is selected from the range of 20 mmHg to 80 mmHg, and may equal any sub-range or individual value within said range. Once adequate stimulation is achieved with a given stimulation sequence, that stimulation sequence becomes fixed and is repeatedly applied to the first electrode pair. In some embodiments, the same process of applying various stimulation sequences is then performed with the next electrode pair $E_2$ until adequate stimulation is achieved. The same process may progress to each subsequent electrode pair in a similar fashion until adequate stimulation is achieved at each pair. In some embodiments, such a method of stimulation achieves a wave of contractions along the esophagus. In some embodiments, the wave induces contractions further along the GI tract, such as, for example, contractions within the stomach, small intestine, and/or large intestine.

Figure 7A:
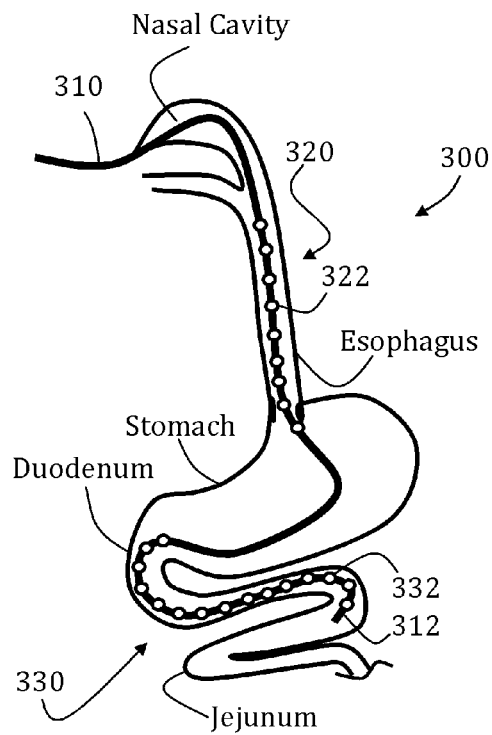
FIGS. 7A-B schematically illustrate exemplary naso jejunal feeding tubes positioned in-place each comprising a plurality of electrodes, in accordance with some embodiments of the present invention.
Figure 7B:
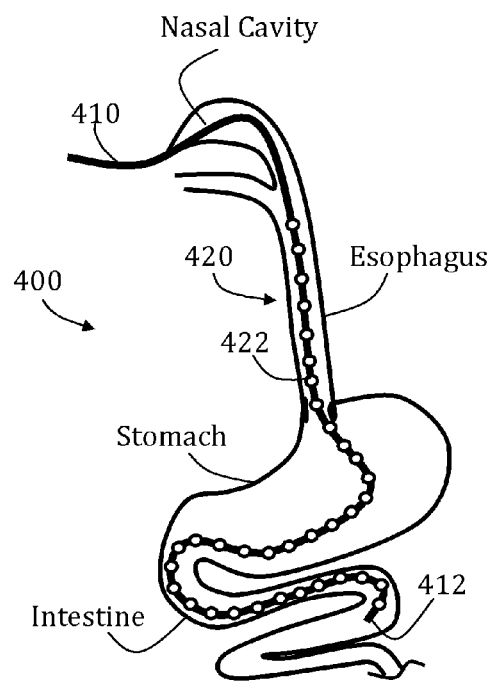

FIGS. 7A-B schematically illustrate exemplary naso-jejunal feeding tubes (300 and 400, respectively) positioned in-place, each comprising a plurality of electrodes, in accordance with some embodiments. Optionally, nasojejunal tubes 300 and/or 400 are configured to evoke GI tract motility in selective anatomic locations and/or organs, for example in esophagus, duodenum, jejunum and/or elsewhere. In FIG. 7A, nasojejunal feeding tube 300 includes intubation 310, along which two distinct arrays of electrodes terminals are provided, namely esophagus array 320 and intestine array 330, in which the esophagus array 320 includes a terminal 322 and intestine array include a terminal 332. If positioned correctly, in some embodiments, such as illustratively suggested in FIG. 7A, intubation 310 extends from nasal cavity, through esophagus, stomach, duodenum and ends with a distal end 312 thereof in the jejunum. In some such embodiments, and as shown, esophagus array 320 is positioned at least partially in the esophagus, whereas intestine array 330 is positioned in the duodenum and at least partially in the jejunum.

In FIG. 7B, nasojejunal feeding tube 400 includes intubation 410, along which a single continuous array of electrodes terminals is provided, namely array 420, which includes a terminal 422. If positioned correctly, in some embodiments, such as illustratively suggested in FIG. 7B, intubation 410 extends from nasal cavity, through esophagus, stomach, duodenum and ends with a distal end 412 thereof in the jejunum. In some such embodiments, and as shown, array 420 is positioned at least partially in the esophagus, loosely or otherwise (and possibly ineffectively) extends in the stomach, and then effectively positioned in the duodenum and at least partially in the jejunum.

Figure 8A:
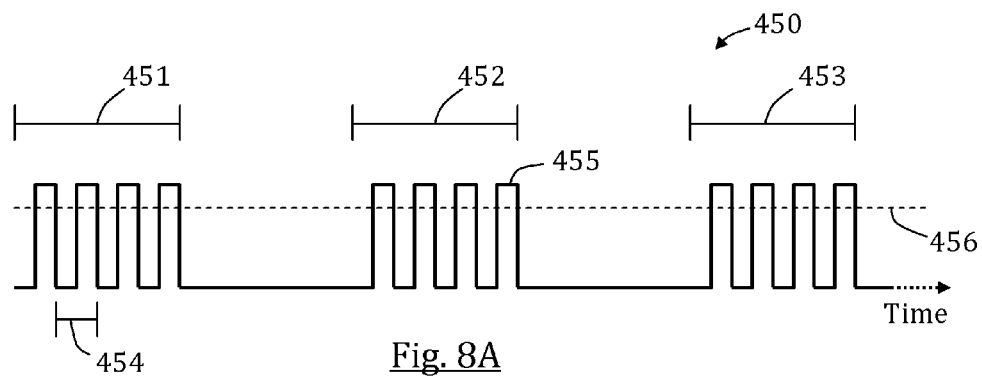
FIGS. 8A-C schematically illustrates exemplary series of pulse trains, in accordance with some embodiments of the present invention.
Figure 8B:
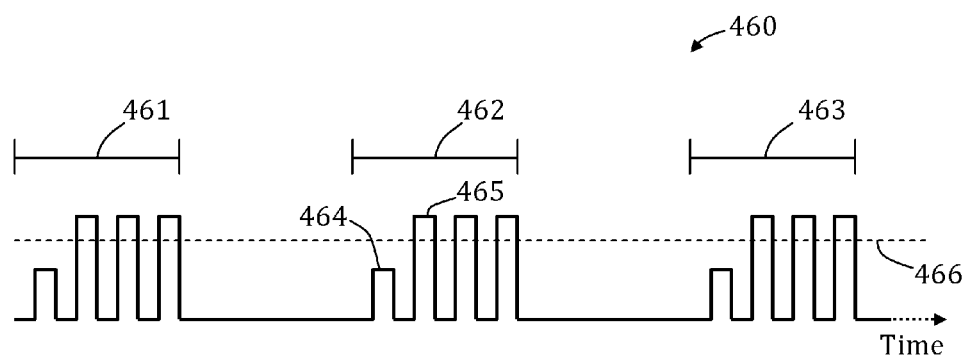
Figure 8C:
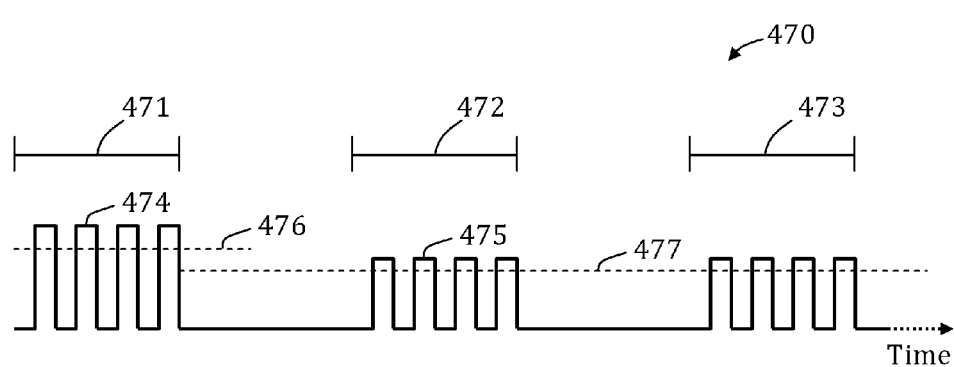

FIGS. 8A-C schematically illustrate exemplary series of pulse trains 450, 460 and 470, respectively, in accordance with some embodiments. Any of series 450, 460 and 470 varies in time according to a chosen frequency and linked to at least one electrodes terminal provided along a motility evoking system according to the present invention, such as any of the exemplary devices described hereinabove, optionally discretely (e.g., if different terminals operate discretely in terms of trains form, magnitudes and/or timing). In FIG. 8A, series 450 shown includes at least three consecutive trains 451, 452, 453, each substantially same in form, magnitude and frequency, for simplified illustrative purposes, although some variance may occur in normal practice. Each train includes a number of cycles, such as cycle 454 in train 451 (shown herein are four cycles in each train for illustrative purposes), each cycle includes a single pulse, such as pulse 455 in train 452. Optionally all cycles and pulses are substantially same in frequency and magnitude. As shown, at least these three trains as part of a possible greater series, each include pulses being greater in magnitude than a stimulation threshold 456 being substantially constant as in some tissue portions along GI tract. Since each pulse train exceeds threshold 456, local tissue in direct contact with and/or adjacent linked operative terminals will be evoked (if normally functional), optionally to a motility pattern such as local contraction (e.g., in case it includes a muscle tissue).

In FIG. 8B, series 460 shown includes at least three consecutive trains 461, 462, 463, each substantially same in form, magnitude and frequency, for simplified illustrative purposes, although some variance may occur in normal practice. Each train includes a number of cycles; each cycle includes a single pulse. Optionally each train includes a first cycle differing from its following cycles in at least magnitude of pulse. As shown in this exemplary illustrative embodiment, in train 462, a first pulse 464 is substantially smaller in magnitude than following pulses (including pulse 465). In some such embodiments, pulse 464 is smaller in magnitude than a stimulation threshold 466 whereas pulse 465 is substantially greater than threshold 466. At least in some tissue portions along GI tract, one or more below-threshold pulses can be applied to prime the tissue and induce it to contract more firmly and efficiently and to begin contracting at lower voltage stimulation levels.

At least in some tissue portions along GI tract, following at least one pulse, optionally at least one train of such pulses, each pulse or pulses being substantially greater than a minimal local stimulation threshold, the minimal local threshold may drop so other following pulses can be smaller in magnitude than the previous one(s), even if they are smaller than the original stimulation threshold, while still evoking local motility. In FIG. 8C, series 470 shown includes at least three consecutive trains 471, 472, 473, each substantially same in form and frequency, for simplified illustrative purposes, although some variance may occur in normal practice; yet differentiated in pulses magnitudes. Each train includes a number of cycles; each cycle includes a single pulse. Optionally, train 471 includes pulses including pulse 474) which substantially greater in magnitude than pulses of consecutive trains 472 and 473 (including pulse 475). In some such embodiments, pulse 474 is greater in magnitude than a first stimulation threshold 476 whereas pulse 475 is substantially smaller than first stimulation threshold 476, yet substantially greater than a second stimulation threshold 477.

It should be understood that different series types, such as ones being similar to any of series 450, 460 and 470, may be combined in any fashion as segments as part of a single continuous series or consecutive series, according to need and/or according to local anatomy function.

In some embodiments, only one or some "heterogeneous" trains (such as train 461 in series 460) may be needed and can be followed by more "homogeneous" trains (such as train 451 in series 450).

In some embodiments, in "heterogeneous" series (such as series 470) at least one train, optionally including at least one "higher-magnitude" train (such as train 471) and/or at least one "lower-magnitude" train (such as train 472), is heterogeneously formed (e.g., similar to train 461 in series 460), optionally comprising pulses differentiated in magnitude.

In some embodiments, at least in some tissue portions along GI tract, stimulation threshold may vary continuously, either in response to previous local stimulation(s) and/or due to different, in-direct or irrelevant causes, so trains and/or pulses may be changed accordingly in order to achieve and/or maintain improved efficiency throughout operation of the motility evoking system. Stimulation threshold variance may be random or purposive (e.g., only drop in time under repetitive stimulations until possibly reaching a minimal asymptote). In some embodiments, means are provided with the motility evoking system which detect local conditions to asses and choose a specified localized stimulation magnitude accordingly. Local conditions may include, in one example, pressure and/or impedance, which may be used in assessing or calculating a discrete minimal stimulation threshold; and/or, in a second example, pH, which may be used in assessing presence of retrograde gastric content. The motility evoking system may include special purpose sensing elements (such as at least one sensor such as in the case of feeding tube 31 shown in FIG. 1C), or may utilize at least some of its stimulation electrodes for sensing local conditions (such as by applying them for measuring impedance). The motility evoking system may be an open-loop system in the sense it is set selectively or semi-automatically by an operator according to need, or it may be a closed-loop system in the sense that it is autonomously controlled by changing stimulation magnitudes and/or other parameters per measured or sensed conditions.

Figure 9:
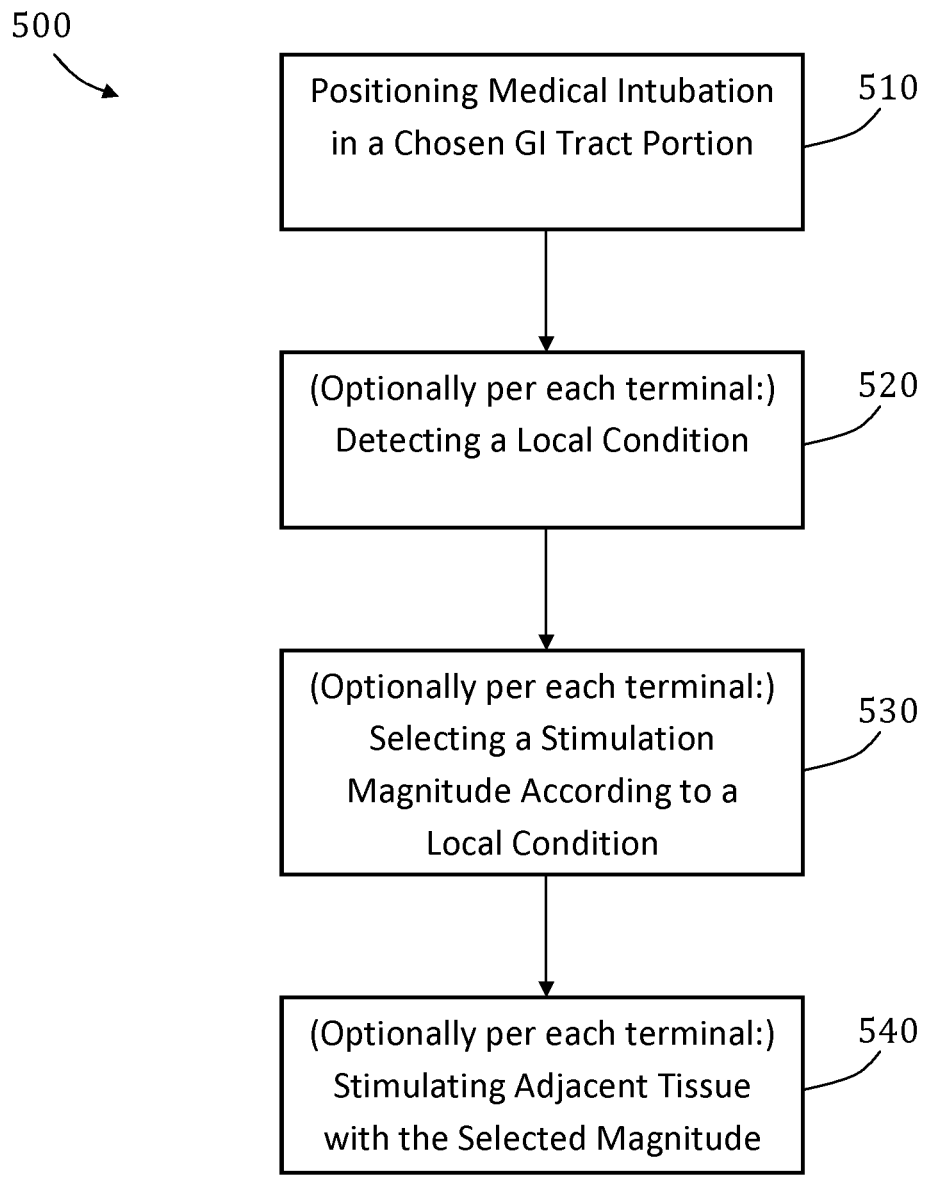
FIG. 9 illustrates steps in an exemplary method for stimulating a chosen GI tract segment, in accordance with some embodiments of the present invention.

FIG. 9 illustrates steps in an exemplary method 500 for stimulating a chosen GI tract segment, in accordance with some embodiments. Method 500 includes positioning 510 a motility evoking system, optionally a medical intubation (nasogastric or nasojejunal), in a chosen GI tract portion. Exemplary systems and/or positioning formations may be as illustratively suggested in any of FIGS. 1A, 1B, 1C, 7A, 7B and 10, or otherwise, according to need. Method 500 may then include detecting 520 a local condition (such as pH, pressure, impedance, electrical resistance, temperature or other or any combination thereof), followed by selecting 530 a stimulation magnitude according to the detected local condition. Selecting 530 may include selecting a minimal evoking current needed to overcome a known or assessed local stimulation threshold, or it may include choosing between stimulating or not stimulating at all at a particular time. Method 500 may then include stimulating 540 adjacent tissue with stimulation having magnitude as selected 530. Any of steps 520 to 540 may be performed separately to each terminal or to each electrode, or it may be performed to some or all terminals or electrodes. Any of steps 520 to 540 may be repeated as needed or as pre-set, optionally continuously, either in same or in different order. The method may optionally include a step of identifying a patient in need of lower GI tract motility. Such patients may include those having muted or less dominant esophageal motility. The method may optionally include monitoring a patient's lower GI tract motility and/or stopping transmitting signals when lower GI tract motility is substantially restored. The detection of a local condition may occur within the esophagus alone. In some embodiments, the GI tract portion is the portion of the esophagus between the UES and the LES.

In some embodiments, the local condition includes the local impedance indicative of an esophageal muscle tissue, optionally more specifically an esophageal smooth muscle tissue. A controller may be configured to allow activation of a generator only when measured local impedance is below about 2,000 ohms, optionally specifically between 500 and 2,000 ohms. The activation may only occur at electrodes in direct contact with and/or adjacent said local measured impedance between 500 and 2,000 ohms. In this way, the system may disregard accurately placing electrodes and allow the measuring unit to choose which electrode to use based on the assessed local anatomy which may be only the lower part of the esophagus between UES and LES containing smooth muscle tissue that is normally located at the lower 67% of esophagus length.

Figure 10:
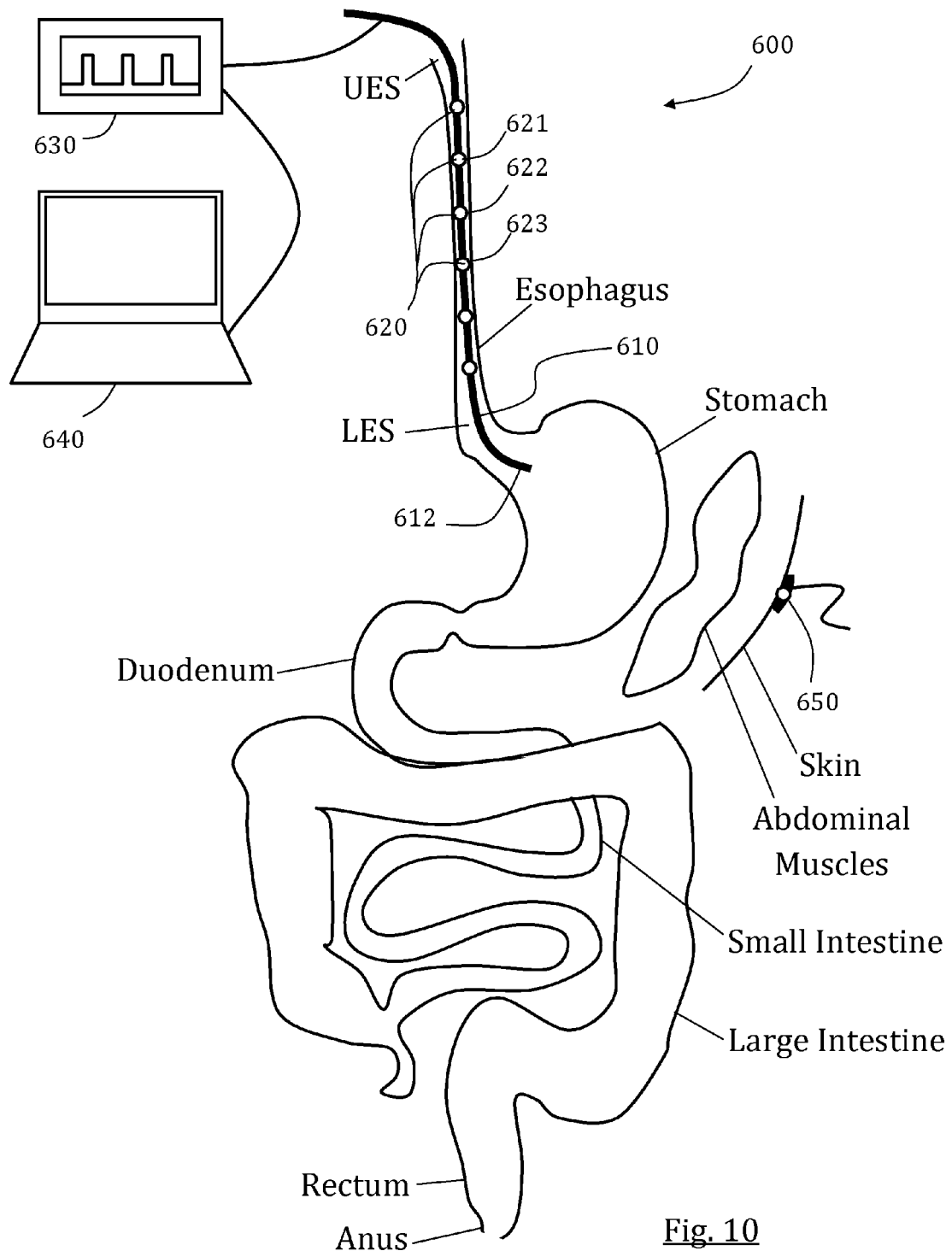
FIG. 10 schematically illustrates an exemplary system with an elongated body positioned in the esophagus and a series of electrodes, programmed for GI tract activation, in accordance with some embodiments of the present invention.

Reference is now made to FIG. 10 which schematically illustrates an exemplary system 600 with an elongated body 610 positioned in the esophagus and a series of electrodes 620, programmed for GI tract activation, in accordance with some embodiments of the present invention. In some embodiments, system 600 is configured for evoking motility in a GI tract portion, optionally a GI tract portion including the esophagus and at least one other region or segment remote from the esophagus. Optionally, the target GI tract portion is located in at least one of the stomach, the small intestine and the large intestine. As shown, no electrodes are positioned in the targeted GI tract portion. Thus, the need for a long tube extending through a patient may be eliminated. As such, one or more organs distal to the LES may be stimulated by a device placed within the esophagus alone. In this way, a safer, less time consuming, and less invasive procedure may be used to stimulate the lower GI tract.

In some embodiments, elongated member 610 is sized and configured for nasal or oral placement in the esophagus. In some embodiments, system 600 comprises a feeding tube, optionally elongated member 610 includes or is the feeding tube. As shown, elongated member 610 includes a distal end protruding in the stomach so in case of a feeding tube embodiment, the feeding tube presented (for illustrative purposes) is a gastric (e.g., nasogastric) feeding tube. Optionally and alternatively, the feeding tube is nasojejunal (not shown).

In some embodiments, electrodes 620 are mounted or mountable on elongated member 610, positioned to stimulate a series of portions of the esophagus between the UES and the LES to evoke local contractions.

In some embodiments, system 600 includes a generator 630 connected to the series of electrodes 620. Optionally, series of electrodes 620 includes at least 3 electrodes of same designated polarity (i.e., negative (−) or positive (+)), optionally at least 4 electrodes of same designated polarity, optionally at least 6 electrodes of same designated polarity, or optionally at least 8 electrodes of same designated polarity, or higher, or lower, or intermediate number. Optionally, all electrodes are spaced apart, optionally evenly spaced apart.

In some embodiments, system 600 includes a control system 640 which comprises a processor and a memory. In some embodiments, control system 640 memory includes preset commands, optionally programmable by a user, for activating generator 630 to generate a signals sequence such that a second electrode 622 is used for transmitting a second signal a first period following a first signal transmitted via a first electrode 621 positioned proximally thereto, and a second period preceding a third signal transmitted via a third electrode 623 positioned distally thereto. In some embodiments, the signals sequence is chosen such to evoke motility in a target GI tract portion located distally to the LES.

In some embodiments, the evoked motility in the target GI tract portion includes a peristalsis. Optionally, the GI peristalsis may begin at a singular point or region and travel downwards (towards the anus), or that different peristalses may begin at different portions or organs in the GI tract, either in parallel or delayed one with the other.

At least one of the first period and the second period is optionally between 0.01 second to 5 seconds, optionally between 0.1 second and 2 seconds, optionally between 0.25 to 0.75 second, optionally equal or less than 0.5 second. In some embodiments, the signals sequence is chosen such to stimulate the series of portions of the esophagus for 0.5 second to 5 minutes, optionally 1 second to 30 seconds, optionally 2 to 20 seconds, optionally 5 to 7 seconds, or higher, or lower or an intermediate value. In some embodiments, the signals sequence is chosen such to evoke distally progressing esophageal contractions. The distally progressing esophageal contractions have a progression velocity of at least 1 cm/second, optionally at least 2 cm/second, optionally at least 3 cm/second, optionally at least 4 cm/second, or higher, or lower, or an intermediate value. Optionally, the signals include a pulse.

In some embodiments, at least one of the first signal, the second signal and the third signal is measured to stimulate a local esophageal contraction of at least 30 mmHg, optionally at least 40 mmHg, optionally at least 50 mmHg, optionally at least 100 mmHg, or higher, or lower, or an intermediate value.

In some embodiments, the distally progressing esophageal contractions are measured to transfer an esophageal content to the stomach, optionally the esophageal content includes at least one of bolus, saliva and gastric refluxate. Optionally, solids and/or liquids are provided to the patient through the mouth and into the esophagus using system 600 or in parallel to its use and the distally progressive esophageal contractions delivers or assists in delivering the solids and/or liquids to the stomach.

In some embodiments, the preset commands are configured for generating a chosen GI tract activation regime with a number of GI tract activating sessions, each including at least one signals sequence. Optionally, the regime and sessions are programmed according to any of patient condition and/or patient dietary and/or diet. For example, the regimen may be selected to mimic a patient's normal eating habits. In some embodiments, GI tract activating sessions may include a stimulation period in the morning, one near mid-day, and one in the evening. Optionally, the regime may include at least 4 separate sessions during a 24 hours period.

In some embodiments, system 600 includes a measuring unit (not shown), optionally mounted on or mountable in or part of elongated member 610, that is configured for measuring a local condition in direct contact with and/or adjacent at least one of the electrodes. Optionally, alternatively or additionally, the measuring unit uses at least two electrodes as measurement electrodes. Optionally, the local condition includes a change in local impedance indicative of gastric refluxate. Optionally, system 600 includes a controller (not shown; or may be embedded or part of control system 640, for selecting a pulse magnitude in accordance with the local condition.

In some embodiments (not shown in this example) electrodes 620 includes at least one electrode configured for delivery within the stomach and optionally for contacting a stomach wall portion. Optionally, such a stomach electrode is positionable to stimulate a stomach wall tissue when elongated member 610 is placed in the esophagus. Optionally, the stomach electrode is mounted or mountable on elongated member 610. In some embodiments, system 600 includes an auxiliary set comprising at least one outer-body electrode 650 for closing an electrical circuit with an implanted electrode (of series 620). Optionally, electrode 650 is positionable to direct contact with patient's skin. In some embodiments, electrode 650, optionally when paired with the esophageally delivered "stomach electrode", is used to stimulate an abdominal muscle tissue thereby evoking contractions thereof.

In some embodiments, generator 630 is configured (optionally by commands pre-set to control system 640, as described above) to generate a series of pulses, which comprising at least one preliminary pulse followed by stimulatory pulses. In some embodiments, the at least one preliminary pulse initiates narrowing (e.g., compressing, collapsing or falling) of an esophageal portion such that an esophageal wall is in contact with at least one electrode 620, thereby lowering a nominal stimulation threshold to a second threshold. In some embodiments, the stimulatory pulses are equal or lower than the nominal stimulation threshold and higher than the second threshold.

In some embodiments, the at least one preliminary pulse is greater in magnitude than a maximal magnitude or an average magnitude of the stimulatory pulses. Optionally and alternatively, the at least one preliminary pulse is smaller in magnitude than a minimal magnitude or an average magnitude of the stimulatory pulses. Optionally, the second threshold is smaller by at least 2 mA (milliamperes) than the nominal stimulation threshold, optionally smaller by approximately 5 mA than the nominal stimulation threshold. Optionally, the nominal stimulation threshold is between 10 mA and 50 mA, optionally between 15 mA and 25 mA, optionally between 18 mA and 22 mA, or higher, or lower, or an intermediate value. Optionally, the series of pulses comprises a first train comprising the at least one preliminary pulse, and a second train comprising the stimulatory pulses. Optionally, alternatively or additionally, the series of pulses comprises at least one train which includes the at least one preliminary pulse and the stimulatory pulses Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference constitutes prior art. To the extent that section headings are used, they should not be construed as necessarily limiting.

What is claimed is:

1. A method for evoking motility in a lower GI tract portion located remote from the esophagus, from within the esophagus, in a subject, the method comprising:
    positioning in the esophagus a GI contraction-stimulation system comprising an elongated member with at least one electrode pair;
    placing a first electrode in each one of said electrode pair adjacent to a respective first portion of an esophageal muscle and electrically connecting said first electrode to a signal generator;
    placing a second electrode in each one of said electrode pair adjacent to a respective second portion of said esophageal muscle and electrically connecting said second electrode to a grounding site;
    powering on said GI contraction-stimulation system; and
    applying said GI contraction-stimulation system to generate an electrically induced signal sequence, repeatedly applied to each one of said at least one electrode pair, thereby causing repeated local contractions of said esophageal muscle between said respective first and respective second portions of said esophageal muscle, until evoking a muscle contraction within the lower GI tract portion resulting from said repeated esophageal muscle contractions.

2. The method of claim 1, wherein said applying said GI contraction-stimulation system includes generating a number of GI tract activating sessions, each including a plurality of sequence cycles, each sequence cycle comprising a single signal sequence and a following sequence intermission.

3. The method of claim 2, wherein a total duration of said single sequence cycle is between 0.5 minute and 5 minutes.

4. The method of claim 3, further comprising feeding the subject, wherein sequence cycles generated during patient feeding are shorter than sequence cycles generated in between feedings.

5. The method of claim 4, wherein sequence cycles generated at night are shorter than sequence cycles generated at day time.

6. The method of claim 1, wherein said applying said GI contraction-stimulation system includes generating a first signal to evoke local muscle contraction at a first electrode pair, and, following a first period, generating a second signal to evoke local muscle contraction at a second electrode pair positioned distally to said first electrode pair.

7. The method of claim 6, wherein said applying said GI contraction-stimulation system further includes, following a second period, generating a third signal to evoke local muscle contraction at a third electrode pair positioned distally to said second electrode pair.

8. The method of claim 7, wherein at least one of said first period and said second period is between 0.1 second and 2 seconds.

9. The method of claim 1, wherein said signal sequence includes a plurality of pulses, wherein said plurality of pulses is applied in a frequency between 5 and 50 Hz, or/and wherein a width of a pulse in said plurality of pulses is between 1 and 20 milliseconds.

10. The method of claim 9, wherein said signal sequence includes a plurality of pulse trains, wherein an intermission between two pulse trains in a single signal sequence is between 0 and 2 seconds.

11. The method of claim 10, wherein the number of said pulse trains is equal or higher than the number of electrodes of same designated polarity in use for applying said pulse trains.

12. The method of claim 1, further comprising measuring impedance values, wherein said applying said GI contraction-stimulation system is continued only upon detected impedance values or a change in impedance value being greater than a threshold value.

13. The method of claim 12, wherein said threshold value is indicative of an esophageal smooth muscle tissue.

14. The method of claim 12, wherein said threshold value is between 500 and 2,000 ohms.

15. The method of claim 1, wherein said positioning includes positioning said at least one electrode pair below UES or/and above LES in the esophagus.

16. The method of claim 1, wherein said GI contraction-stimulation system further comprises a generator, a processor, and a memory, wherein said memory stores preset commands configured for activating said generator, to thereby generate said signal sequence.

17. The method of claim 1, comprising stimulating series of portions of the esophagus for 2 to 20 seconds.

18. The method of claim 1, further comprising stimulating a stomach wall tissue, following said positioning of said elongated member.

19. The method of claim 1, wherein said applying said GI contraction-stimulation system generates said at least one signal sequence for a duration of at least 15 minutes, thereby evoking motility in a target GI tract portion located distally to the LES.

* * * * *